US012582436B2

(12) United States Patent
Gowda et al.

(10) Patent No.: US 12,582,436 B2
(45) Date of Patent: Mar. 24, 2026

(54) EXTERNAL NEEDLE GUIDE AND ANCHOR

(71) Applicant: VOYAGER BIOMEDICAL, INC.,
Houston, TX (US)

(72) Inventors: Ashok Gowda, Houston, TX (US);
Kimberly Marie Neely, Houston, TX
(US); Charles Houssiere, Houston, TX
(US); Alan Glowczwski, College
Station, TX (US); **Justin Lynn
Glowczwski**, Austin, TX (US)

(73) Assignee: Voyager Biomedical, Inc., Houston,
TX (US)

( * ) Notice: Subject to any disclaimer, the term of this
patent is extended or adjusted under 35
U.S.C. 154(b) by 0 days.

(21) Appl. No.: 17/427,241

(22) PCT Filed: Feb. 22, 2021

(86) PCT No.: PCT/US2021/019076
§ 371 (c)(1),
(2) Date: Jul. 30, 2021

(87) PCT Pub. No.: WO2021/168428
PCT Pub. Date: Aug. 26, 2021

(65) Prior Publication Data
US 2022/0039831 A1      Feb. 10, 2022

Related U.S. Application Data

(60) Provisional application No. 62/980,036, filed on Feb.
21, 2020.

(51) Int. Cl.
*A61B 17/34*       (2006.01)
*A61B 17/00*       (2006.01)

(52) U.S. Cl.
CPC ... *A61B 17/3403* (2013.01); *A61B 2017/00893*
(2013.01); *A61B 2017/00951* (2013.01);
(Continued)

(58) Field of Classification Search
CPC ...... A61B 17/3403; A61B 2017/00893; A61B
2017/00951; A61B 2017/3407;
(Continued)

(56) References Cited

U.S. PATENT DOCUMENTS 3,973,565 A    8/1976   Steer
4,250,880 A    2/1981   Gordon
(Continued)

FOREIGN PATENT DOCUMENTS

AU       2001275058       2/2002
CA       2281457  A1      2/2001
(Continued)

OTHER PUBLICATIONS

International Search Report and Written Opinion issued in International Application No. PCT/US2021/019076, mailed May 5, 2021, 12 pages.
(Continued)

*Primary Examiner* — Anh T Dang
(74) *Attorney, Agent, or Firm* — Talem IP Law, LLP

(57) ABSTRACT

An external needle guide can include a skin contact portion for attaching to skin of a patient and a needle guide portion for guiding a needle into a vessel of the patient. The external needle guide provides an accurate placement of a needle into the vessel (e.g., a good puncture), which reduces the failures of the vessel. Furthermore, because of the accurate placement of the needles and the ease of placement of the external needle guide, a patient and/or another person can insert the needles into the vessel with one hand. An external needle guide can also include an anchor portion that secures a needle to the external needle guide, preventing unwanted movement of the needle and damage to the vessel.

9 Claims, 34 Drawing Sheets

(52) U.S. Cl.
CPC ................. *A61B 2017/3407* (2013.01); *A61B 2017/3411* (2013.01)

(58) Field of Classification Search
CPC ... A61B 2017/3411; A61M 2025/0253; A61M 2025/0266
See application file for complete search history.

(56) References Cited

U.S. PATENT DOCUMENTS

| | | | | |
|---|---|---|---|---|
| 4,863,432 A | * | 9/1989 | Kvalo .................. | A61M 25/02 604/177 |
| 5,722,959 A | * | 3/1998 | Bierman ............... | A61M 25/02 604/174 |
| 5,911,707 A | | 6/1999 | Wolvek et al. | |
| 8,105,290 B2 | | 1/2012 | Wright et al. | |
| 2006/0084922 A1 | | 4/2006 | Botha | |
| 2007/0265571 A1 | | 11/2007 | Utterberg et al. | |
| 2008/0154205 A1 | | 6/2008 | Wojcik | |
| 2009/0306591 A1 | | 12/2009 | Amisar et al. | |
| 2010/0179482 A1 | | 7/2010 | Wright et al. | |
| 2012/0232488 A1 | | 9/2012 | Aviles | |
| 2013/0150714 A1 | | 6/2013 | Howlett et al. | |
| 2015/0367085 A1 | | 12/2015 | Ravikumar et al. | |

FOREIGN PATENT DOCUMENTS

| | | | |
|---|---|---|---|
| EP | 0261835 | A2 | 3/1988 |
| JP | S6382674 | A | 4/1988 |
| JP | 200670744 | | 10/1994 |
| JP | H10512177 | A | 11/1998 |
| JP | 2002526177 | A | 8/2002 |
| JP | 2006070744 | A | 3/2006 |
| JP | 2007136268 | A | 6/2007 |
| JP | 2007519424 | A | 7/2007 |
| JP | 2008100054 | A1 | 5/2008 |
| JP | 2014500129 | A | 1/2014 |
| JP | 2014519959 | A | 8/2014 |
| WO | 9715337 | A1 | 5/1997 |
| WO | 0020065 | A1 | 4/2000 |
| WO | 2007133436 | A2 | 11/2007 |

OTHER PUBLICATIONS

Office Action issued in European Patent Office Application No. 21757196.7, mailed May 28, 2024, 5 pages.
Office Action issued in Japanese Application No. 2022-549991, mailed Dec. 9, 2024, 21 pages.

* cited by examiner

100

124

110

120

122

100

110

112

114

1000

1000

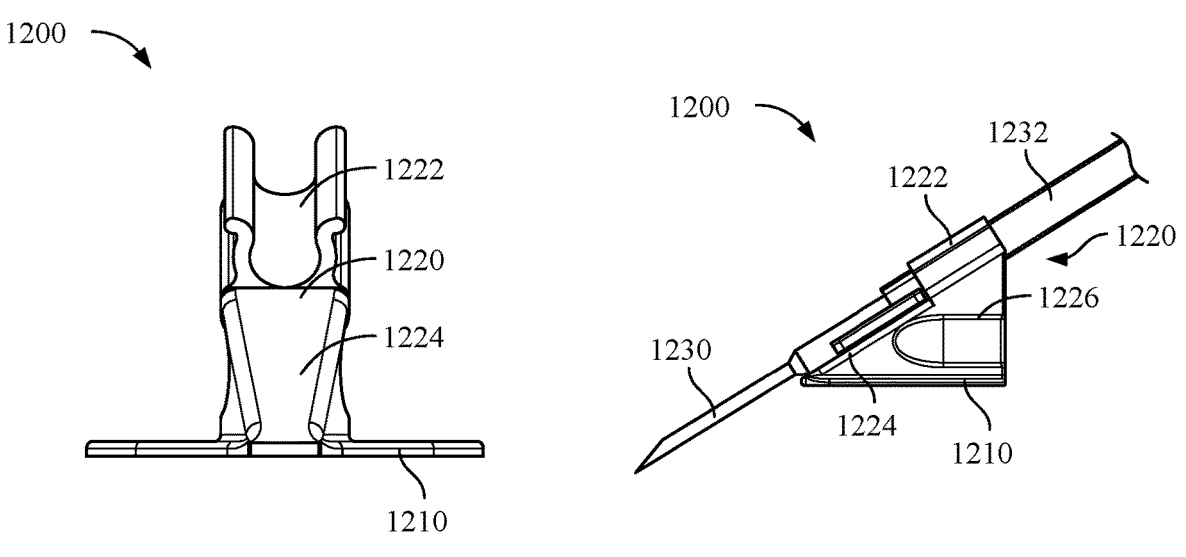
FIG. 12A　　　　　　FIG. 12B
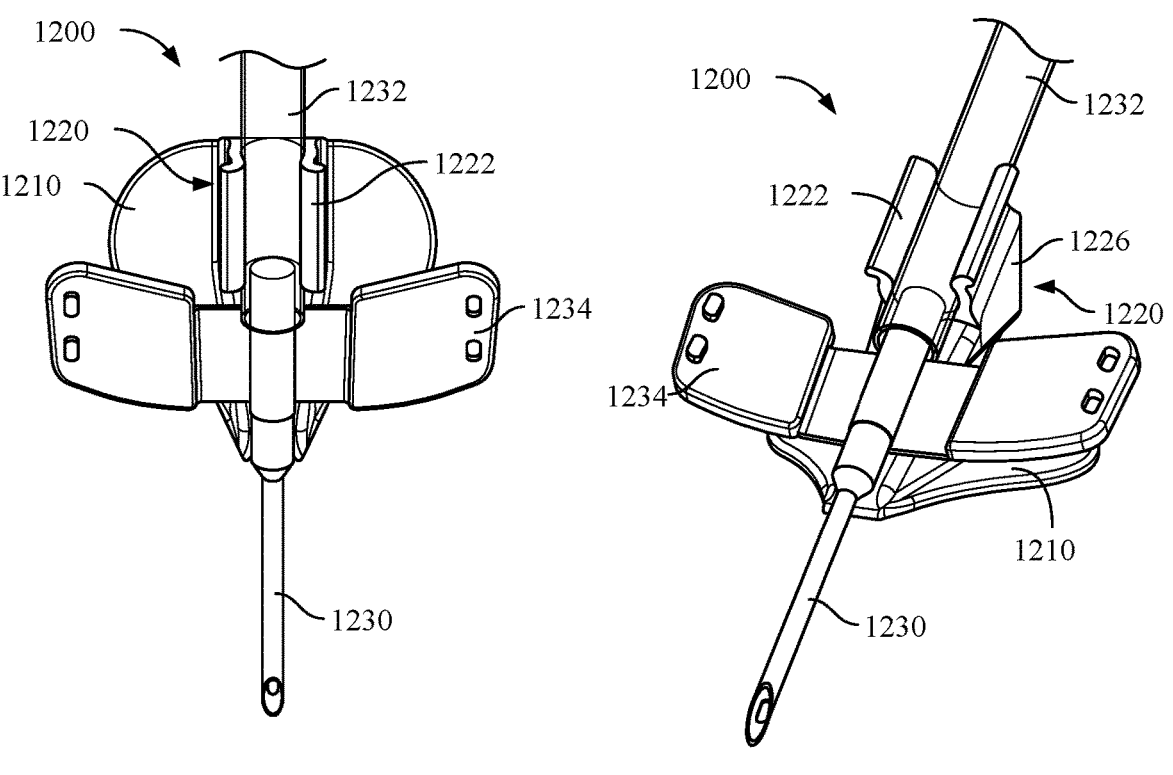
FIG. 12C　　　　　　FIG. 12D

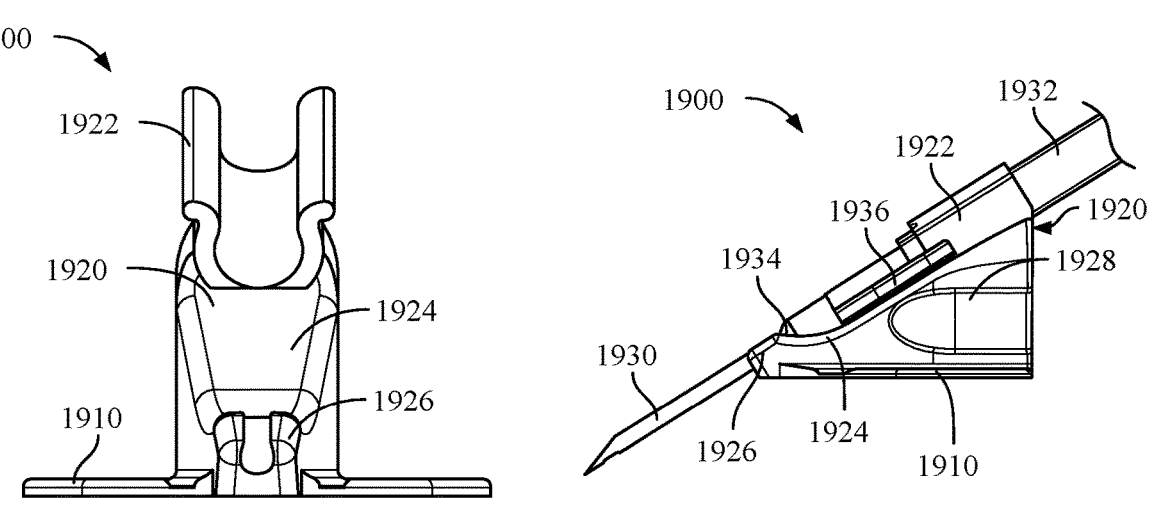
FIG. 19A          FIG. 19B
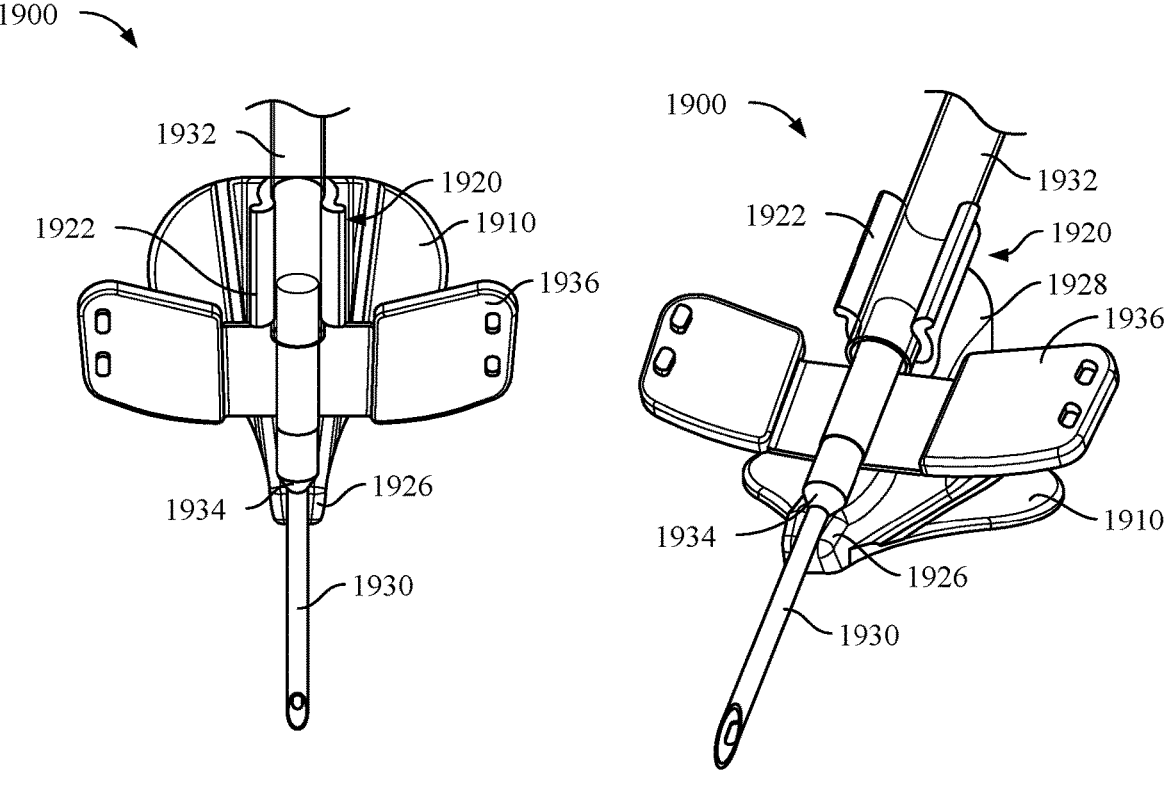
FIG. 19C          FIG. 19D

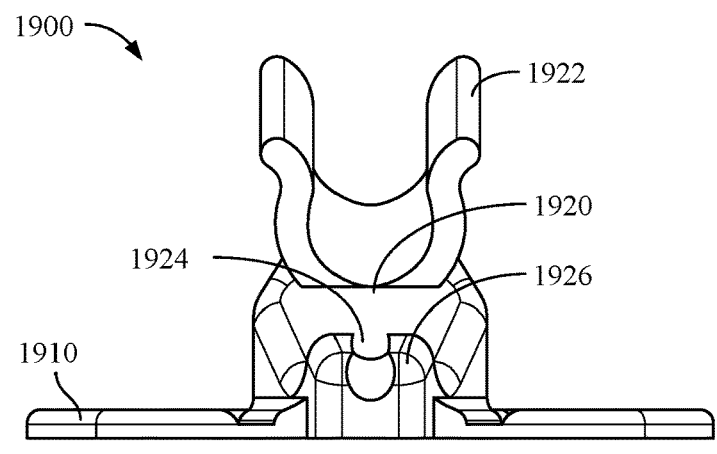
FIG. 19E
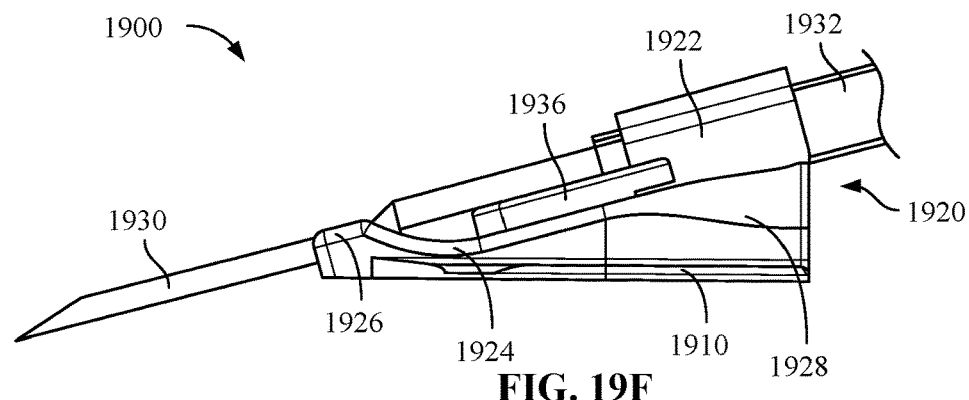
FIG. 19F
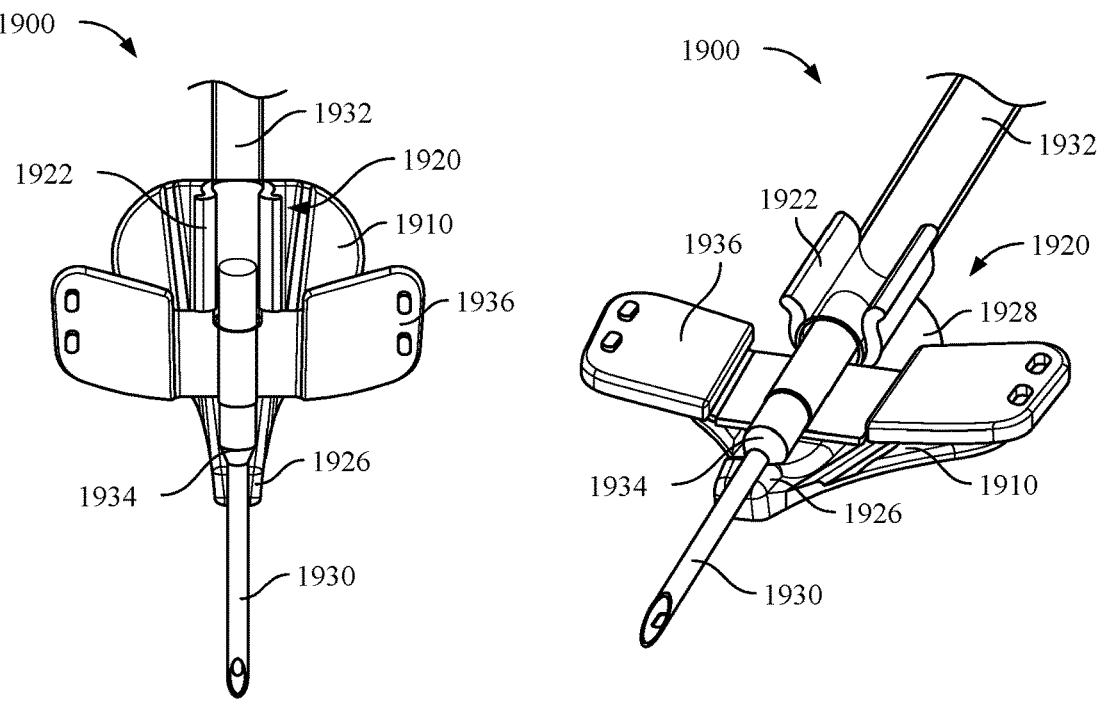
FIG. 19G                         FIG. 19H

EXTERNAL NEEDLE GUIDE AND ANCHOR

CROSS-REFERENCE TO RELATED APPLICATIONS

This application is the U.S. National Stage Application of International Application No. PCT/US21/19076, filed Feb. 22, 2021, which claims the benefit of U.S. Provisional Patent Application Ser. No. 62/980,036, filed Feb. 21, 2020, which are hereby incorporated by reference in their entirety.

BACKGROUND

Every year, millions of people in the United States and around the world require access to vessels for medical treatment, such as dialysis, chemotherapy, drug delivery, or diagnostic procedures (e.g., monitoring levels of components in the blood). Dialysis removes waste, salt, and excess water from the blood to prevent a toxic build-up in the body. Dialysis also helps to maintain a safe level of chemicals in the blood (e.g., potassium, sodium, and bicarbonate) as well as help control the person's blood pressure. Approximately half a million Americans are on dialysis alone. Chemotherapy is used to treat cancers by attacking the fast growing cells associated with the cancer. Chemotherapy and other drug delivery may involve repeated access to vessels over time for medical treatment.

Currently, the most common method of obtaining access to vessels is to identify the vessel by visual inspection or feel. In some cases, a tourniquet can be applied above the desired vessel (e.g., around the bicep when access to a vessel in the elbow region of a patient is desired), causing the vessel to engorge and making it easier to identify through visual inspection. In any case, these methods sometimes require multiple attempts to access the vessel. For people who regularly require access to vessels for medical treatment, repeated access to the vessel can damage said vessel—with even more damage likely when there is a challenge finding the vessel. For instance, those requiring dialysis often have to have dialysis performed several times per week.

Furthermore, once a needle is successfully inserted into a vessel of a patient, large amounts of tape/adhesive may be required to secure the needle and prevent the needle from being accidentally removed, which in the end may not even work. This leads to extra waste, as well as the potentially painful process of removing the tape/adhesive from the patient. Indeed, the process of removing tape/adhesive from the patient not only has the potential to rip hair from the patient's skin, but may also increase the chances of a hematoma in and around the patient's vessel (e.g., due to patient/technician error in removing the tape/adhesive while the needle is still in the patient's vessel).

BRIEF SUMMARY

External needle guides and anchors are provided to facilitate an accurate placement of one or more needles into a vessel (e.g., a good puncture), which reduces the failures of the vessel or inadvertent patient discomfort from needle misses (e.g., a bad puncture), as well as facilitate relatively easy and painless securement of a needle for intravenous medical treatment. As mentioned above, vessels, especially those used for dialysis, may be repeatedly punctured for medical treatment. Repeated punctures at the same location in the vessel often leads to a failure of that vessel, especially when the puncture is a bad puncture. Advantageously, the described external needle guides and anchors can help prevent damage to a vessel (including those supported by an AV fistula) and therefore prevent or at least minimize likelihood of invasive and redundant surgeries. External needle guides and anchors can also function as a needle "anchor" by stabilizing the needle after insertion into a vessel to prevent unwanted movement of the needle tip and avoiding dislodgement of the needle. Indeed, as will become apparent throughout the specification, external needle devices may include needle guide capabilities, needle anchor capabilities, or both.

Furthermore, because of the accurate placement of the needles and the ease of placement of the described external needle guides, a patient and/or other person (e.g., a technician) may be able to insert the needles into the vessel with one hand. For example, a patient may have medical treatment requiring cannulation of the vessels in the arm, neck, groin, leg, or other suitable region of a patient's body. By being able to position and secure the external needle guide with one hand, as well as self-cannulate with one hand, the patient can ensure successful cannulation without the help of another person. This enables a patient to provide themselves with in-home medical treatment, such as dialysis, without the fear of damaging the vessel through excessive and bad punctures.

According to various implementations, an external needle guide includes a skin contact portion for attaching to skin of a patient and a needle guide portion for guiding a needle into a vessel of the patient. The needle guide portion can include at least one needle marker, needle slot, needle notch, and/or needle aperture. In some embodiments, the needle guide portion includes features to secure the needle within the needle guide, preventing inadvertent dislocating of the needle.

In some cases, the external needle guide can include a hinge coupling the skin contact portion to the needle guide portion. The hinge can be configured to enable the needle guide portion to be placed over the skin contact portion. In some cases of the hinge configuration, the needle guide portion can include at least one needle slot having a predetermined or adjustable angle relative to the skin of the patient when placed over the skin contact portion. In some of these cases, the at least one needle slot is two needle slots, and the predetermined angle of one of the two needle slots is a positive acute angle relative to the skin of the patient and the predetermined angle of another one of the two needle slots is a positive obtuse angle relative to the skin of the patient. In some of these cases, the at least one needle slot is a plurality of needle slots, and the predetermined angle of at least one of the plurality of needle slots is a positive acute angle relative to the skin of the patient and the predetermined angle of at least one other one of the plurality of needle slots is a positive obtuse angle relative to the skin of the patient. In some cases, the needle guide portion can include at least one needle notch having a predetermined angle relative to the skin of the patient when placed over the skin contact portion. In some of these cases, the at least one needle notch is two needle notches, and the predetermined angle of one of the two needle notches is a positive acute angle relative to the skin of the patient and the predetermined angle of another one of the two needle notches is a positive obtuse angle relative to the skin of the patient. In some of these cases, the at least one needle notch is a plurality of needle notches, and the predetermined angle of at least one of the plurality of needle notches is a positive acute angle relative to the skin of the patient and the predetermined angle of at least one other one of the plurality of needle notches is a positive obtuse angle relative to the skin of the patient.

In some cases, the external needle guide further includes a needle guide slide having at least one needle marker indicating placement for a needle. In these cases, the skin contact portion includes a guide slot receiving the needle guide slide and enabling the needle guide slide to be positioned over an opening in the skin contact portion. In some of these cases, the at least one needle marker is at least one needle slot.

In some cases, the needle guide portion includes at least one needle slot having a tapered structure that inhibits a needle from being inserted past a predetermined depth into the skin of the patient. In some cases, the needle guide portion includes at least one needle slot having a catch structure to inhibit a needle from being inserted past a predetermined depth into the skin of the patient. In some cases, the needle guide portion can include at least one needle slot having an adjustable angle relative to the skin of the patient. In some cases, the skin contact portion includes a central region having an opening. In some cases, the opening has a size enabling a finger to pass therethrough. In some cases, the skin contact portion further includes a flexible barrier disposed over the opening. In some cases, the flexible barrier may include a slit. In some cases, the needle guide portion includes at least one needle marker indicating placement for a needle on the flexible barrier. In some cases, the at least one needle marker is at least one needle slot. In some cases, the at least one needle marker is at least one needle notch.

In some cases, the skin contact portion comprises an adhesive. In some cases, the skin contact portion comprises a local anesthetic. In some cases, the skin contact portion includes an elongated body having a first end, a second end, and a middle portion. In these cases, the needle guide portion includes at least one needle notch positioned along an edge of the middle portion of the elongated body.

An external needle anchor includes a skin contact portion for securely attaching to skin of a patient and a needle anchor portion for securely holding a needle in place once inserted into a vessel of a patient. In some cases, the needle anchor portion includes corresponding slots on each side of the needle anchor portion for securely holding wings of the needle. In some cases, the skin contact portion includes an adhesive. In some cases, a portion of the adhesive of the skin contact portion is configured to be folded towards the needle once inserted into the vessel of the patient for securely attaching to the skin of the patient. In some cases, the adhesive of the skin contact portion includes wings that extend horizontally from the needle anchor portion. In some cases, the adhesive of the skin contact portion includes an ovular shape. In some cases, the skin contact portion includes an arcuate edge for inserting the needle through the skin of the patient and into the vessel of the patient.

In some cases, the needle anchor portion includes an angle feature for supporting the needle at a particular angle. In some cases, the needle anchor portion further includes a tubing clip for securing a tubing coupled to the needle. In some cases, the needle anchor portion includes a plurality of tubing slots for securing a tubing coupled to the needle, each tubing slot having a different predetermined angle relative to the skin of the patient. In some cases, the needle anchor portion includes a plurality of ridges for securing a tubing coupled to the needle. In some cases, the ridges are in lines at intervals perpendicular to the skin of the patient. In some cases, the ridges are in lines at intervals parallel to the skin of the patient. In some cases, the external needle anchor further includes a needle slot coupled to the needle anchor portion.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIGS. 12A-12H illustrate an implementation of an external needle anchor with an angle feature and a tubing clip.

FIGS. 19A-H illustrate examples of external needle guides/anchors with an angle feature, a needle slot, and a tubing clip.

DETAILED DESCRIPTION

Figure 1A:
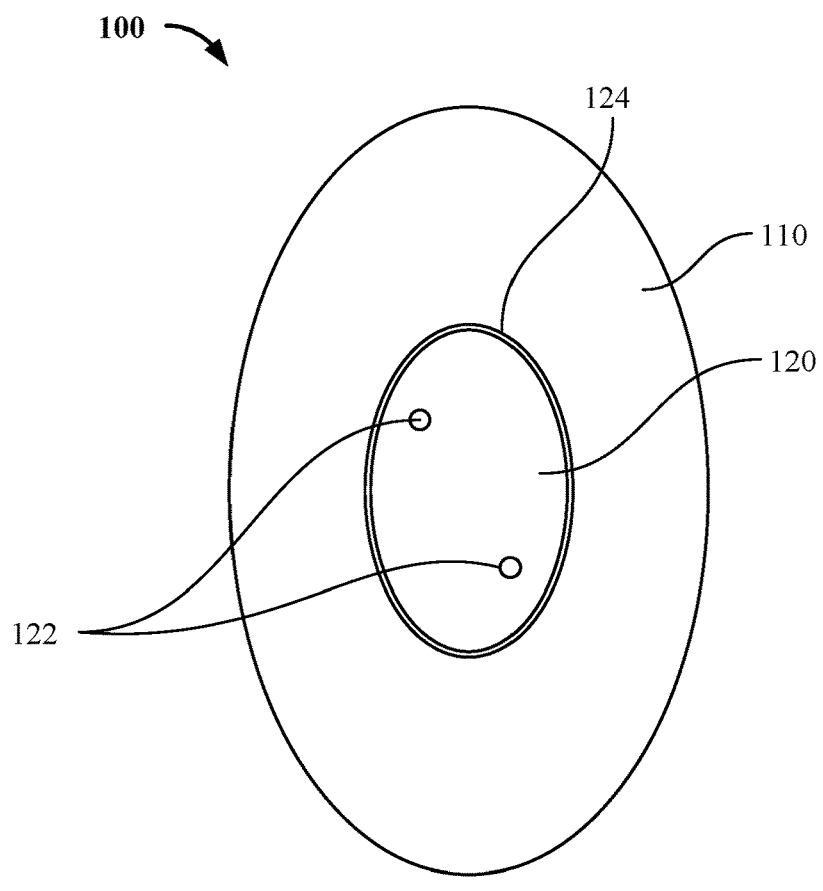
FIG. 1A is a top view illustrating an example of an external needle guide.

External needle guides and anchors are provided to facilitate an accurate placement of one or more needles into a vessel (e.g., a good puncture), which reduces the failures of the vessel or inadvertent patient discomfort from needle misses (e.g., a bad puncture), as well as facilitate relatively easy and painless securement of a needle for intravenous medical treatment. As mentioned above, vessels, especially those used for dialysis, may be repeatedly punctured for medical treatment such as dialysis. Repeated punctures the same location in the vessel often leads to a failure of that vessel, especially when the puncture is a bad puncture. Advantageously, the described external needle guides and anchors can help prevent damage to a vessel (including those supported by an AV fistula) and therefore prevent or at least minimize likelihood of invasive and redundant surgeries. External needle guides and anchors can also function as a needle "anchor" by stabilizing the needle after insertion into a vessel to prevent unwanted movement of the needle tip and avoiding dislodgement of the needle. Indeed, as will become apparent throughout the specification, external needle devices may include needle guide capabilities, needle anchor capabilities, or both.

Furthermore, because of the accurate placement of the needles and the ease of placement of the described external needle guides, a patient and/or other person may be able to insert the needles into the vessel with one hand. For example, a patient may have medical treatment requiring cannulation on the bicep region of their arm. By being able to position and secure the external needle guide with one hand, as well as self-cannulate with one hand, the patient can ensure successful cannulation without the help of another person. This enables a patient to provide themselves with in-home medical treatment, such as dialysis, without the fear of damaging the vessel through excessive and bad punctures.

As used herein, "successful cannulation" or a "good puncture" refers to when a needle/cannula is placed in a vessel to provide access and does not damage any tissue any more than necessary to be placed in the vessel.

As used herein, "unsuccessful cannulation" or a "bad puncture" refers to when a needle/cannula damages more tissue than necessary to be placed in the vessel, whether the needle/cannula is actually placed in the vessel (or not) and/or enters an AV fistula and/or artery. Examples of a bad puncture include when a needle/cannula goes into the vessel and out the back wall of the vessel, or when the vessel is missed altogether, both of which can damage the vessel and/or the tissue surrounding the vessel and can contribute to the collapse of the vessel or even the AV fistula (if applicable). Such a bad puncture can cause blood loss into the surrounding tissue and formation of a hematoma, and cause major discomfort to the patient. Another example of a bad puncture includes when a needle/cannula enters the artery, which can be dangerous if any air (e.g., an air bubble) from the needle/cannula enters the artery, which can lead to an air embolism.

As described herein, an external needle guide generally refers to embodiments that provide the ability to guide a needle/cannula into the vessel. An external needle anchor generally refers to embodiments that provide the ability to anchor/secure the needle/cannula after the needle has been inserted into the vessel. Both an external needle guide and an external needle anchor provide the ability to securely attach to the skin of a patient. In some cases, an external needle guide includes needle anchor features; and in some case, an external needle anchor includes needle guide features. In some cases, an external needle guide does not include any needle anchor features; and in some case, an external needle anchor does not include any needle guide features.

Figure 1B:
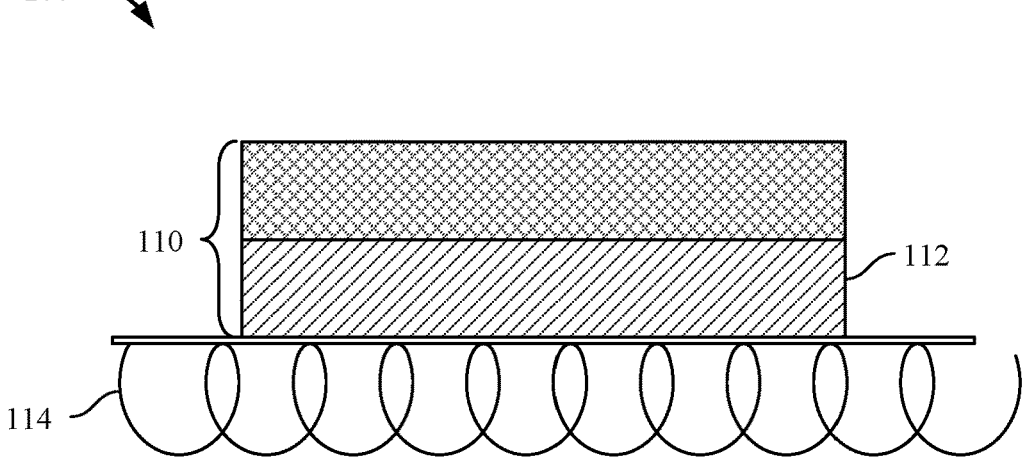
FIG. 1B is a cross-sectional view illustrating an example of an external needle guide.

FIG. 1A is a top view illustrating an example of an external needle guide. FIG. 1B is a cross-sectional view illustrating an example of an external needle guide. As can be seen, an external needle guide 100 can include a skin contact portion 110 and a needle guide portion 120. The skin contact portion 110 includes an adhesive 112 for attaching the skin contact portion 110 onto the skin 114 of a patient.

The needle guide portion 120 can include a guide, such as in the form of needle markers 122, that is used for directing placement of one or more needles into a vessel of the patient. As used herein, a "needle marker" refers to any indicator for a needle insertion point. In some cases, the needle marker is a simple visual marking (two-dimensional) of a needle insertion point; in other instances, the needle marker includes more complex structures that can be used for positioning a needle into a vessel of a patient, such as a needle aperture, a needle slot, and/or a needle notch, which are described below. As used herein, a "needle aperture" refers to an aperture (two dimensional) formed within material of the needle guide portion in which the needle is inserted into the vessel of the patient. Needle markers 122 can be used to correctly position needles through the skin 114 of the patient. The needle markers 122 are contained with a central region 124 of the skin contact portion 110. In some cases, the central region 124 may be made of a deformable material, such that a patient and/or another person using the external needle guide 100 can feel for a palpable indication of a vessel or other structure underneath the skin 114 of the patient. For example, the patient may have previously had a vascular port implanted around a vessel; and that vascular port may be palpable by feeling the skin 114 of the patient. Therefore, the central region 124 may contain deformable material so that the vascular port (which surrounds the vessel) may be located. It should be understood that palpable indications of a location of a vessel may exist other than a palpable vascular port underneath the skin 114 of the patient. For example, scaring around a vessel of the patient may be palpable through the central region 124.

In some cases, the central region 124 includes an opening (e.g., via slits in a material making up the central region) so that a finger (e.g., of the patient and/or another person) can be placed therethrough to find the palpable indication of the vessel of the patient. In other cases, the central region 124 may not contain any material at all so that so that a finger of the patient and/or another person can be placed therethrough to find the palpable indication of the vessel of the patient.

The external needle guide 100 may be made, at least partially, of a rigid material to prevent the skin contact portion 110 from becoming dislodged, for example, when a patient moves; as well as to, for example, provide structure for the patient and/or another person to secure a body of a needle thereto during dialysis.

As mentioned above, the needle markers 122 are used to correctly position needles through the skin 114 of the patient. The placement/arrangement of these markers 122 are configured at positions and distances to facilitate safe entering of a vessel.

Figure 2A:
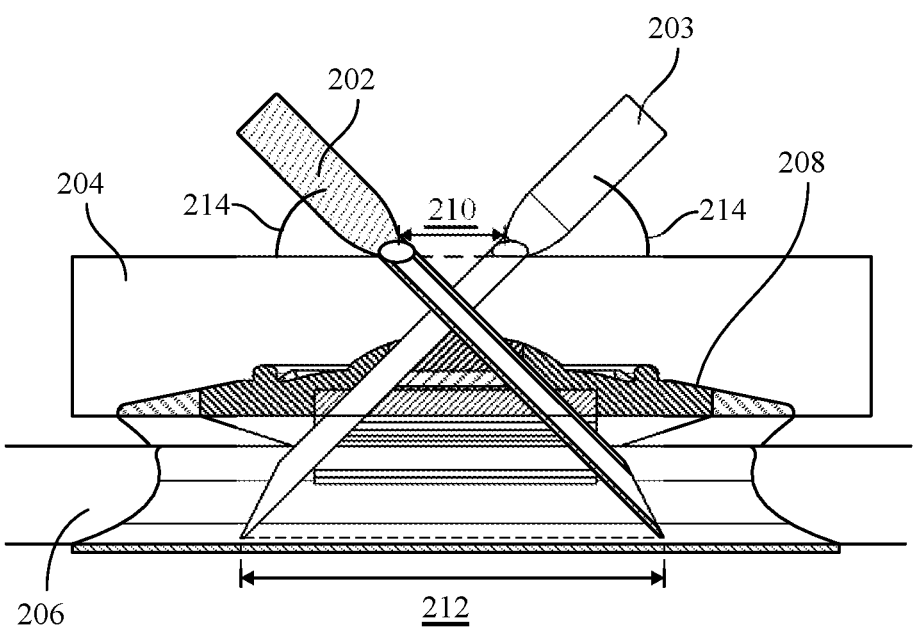
FIGS. 2A and 2B illustrate cross-sections of needles entering a vessel with different distances between needle entry points and needle tips.
Figure 2B:
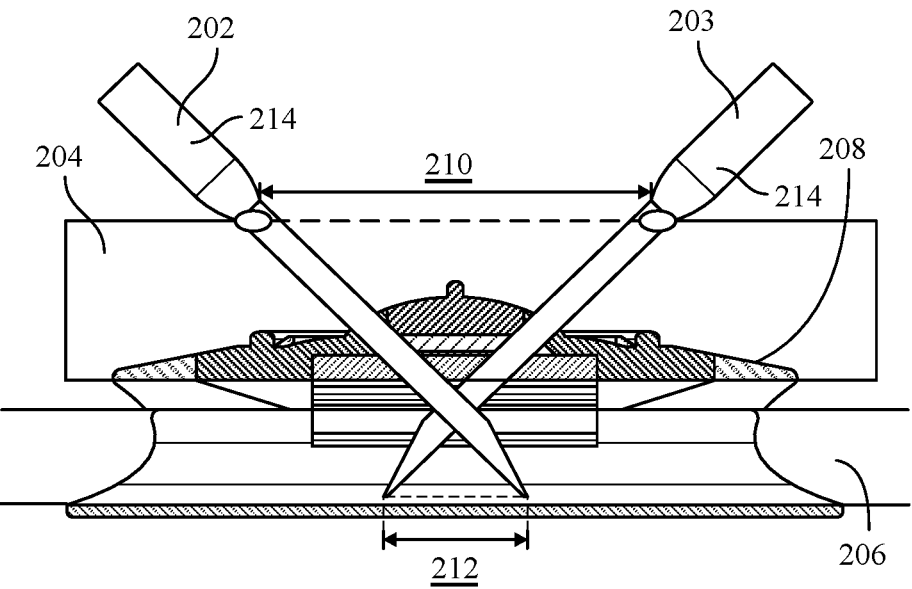

FIGS. 2A and 2B illustrate cross-sections of needles entering a vessel with different distances between needle entry points and needle tips. In the illustrated example, two needles 202, 203 are inserted through the skin 204 of a patient and into a vessel 206 of the patient. In this example, the vessel 206 is surrounded by a vascular port 208. FIGS. 2A and 2B also illustrate the relationship between the distance 210 between needle entry points and the distance 212 between the tips of the needles once inserted into the vessel 206 of the patient. For example, the larger the distance 210 between needle entry points, the smaller the distance 212 between the tips of the needles; and the smaller the distance 210 between needle entry points, the larger the distance 212 between the tips of the needles. In other words, if the angles 214 at which the needles are inserted relative to the skin 204 of the patient remain the same, the distance 210 between needle entry points and the distance 212 between the tips of the needles have an inverse relationship.

Similarly, the depth of the vessel 206 from the skin 204 of the patient and the angles 214 at which the needles are inserted relative to the skin 204 of the patient have a direct relationship (assuming the distance 212 between the tips of the needles is constant). If the depth of the vessel 206 increases, the angles 214 at which needles are inserted relative to the skin 204 of the patient increases; if the depth of the vessel 206 decreases, the angles at which needles are inserted relative to the skin 204 of the patient decreases.

Furthermore, as can be seen, the angles 214 at which the needles are inserted relative to the skin 204, if measured from the right of the entry points, can be said to be a positive acute angle relative to the skin 204 of the patient and a positive obtuse angle relative to the skin 204 of the patient.

If a patient is undergoing dialysis treatments, blood is withdrawn in an upstream portion of the vessel 206 and returned in a downstream portion of the vessel 206. The minimum distance 212 required between the tips of the needles must be enough such that recirculation (e.g., already cleaned blood being recirculated back to through the dialysis machine) does not occur. Because the minimum distance 212 between the tips of the needles is generally a fixed number (e.g., two inches), the angles 214 at which the needles are inserted relative to the skin 204 of the patient may be calculated if the depth of the vessel 206 from the skin 204 of the patient is known.

As a specific example, if the distance 212 between the tips of the needles is required to be at least one inch, and the depth of the vessel from the skin of the patient is also one inch, then one needle will be placed 45 degrees relative to the skin 204 of the patient (e.g., positive acute angle) and the other needle will be placed 135 degrees relative to the skin 204 of the patient (e.g., positive obtuse angle). As is understood by those having ordinary skill in the art, the angles 214 relative to the skin 204 of the patient in which the needles are inserted into the vessel 206 can be deduced through simple geometrical calculations to ensure that the minimum distance 212 between the tips of the needles adhered to. Furthermore, once these calculations are performed, the minimum distance 210 between needle entry points can be made known to the patient/other person. Therefore, the patient/other person can utilize external needle guides having that minimum distance 210 for needle point entry guided by the needle guide portion (via needle markers, needle notches, and/or needle slots as will be described in detail herein).

In any case, a patient and/or another person can determine the angle needed to be used to reach the desired vessel by using the formula:

$$\theta = \sin^{-1}\left(\frac{\text{Depth of the desired vessel}}{\text{Length of the needle inserted through the skin of the patient}}\right).$$

It should be understood that the "Length of the needle inserted through the skin of the patient" does not include the length of the needle that is not inserted through the skin of the patient. For example, if the needle is 1.25 inches long and 0.1 inches of the needle will not be inserted through the skin of the patient, than the "Length of the needle inserted through the skin of the patient" is equal to 1.15 inches (e.g., because 1.25 inches−0.1 inches=1.15 inches). Furthermore, some implementations (e.g., including, but not limited to needle slots, needle apertures, and needle notches) can keep the length of the needle that is not inserted through the skin of the patient constant by inhibiting a needle from being inserted past a predetermined depth into the skin of the patient, making calculations even easier for patients and/or other persons.

For example, if a patient knows that the depth of the vessel they wish to access is 0.6 inches from the surface of their skin and they are utilizing a 1.5 inch needle, the patient can either select a needle guide with a fixed angle feature (e.g., including, but not limited to needle slots, needle apertures, and needle notches) or adjust a needle guide with an adjustable angle feature to approximately 30 degrees relative to the skin of the patient to cannulate the desired vessel $$\left(\text{e.g., because } \sin^{-1}\left(\frac{0.6}{1.25}\right) = \sim 29.5°;\right.$$

assuming 0.25 inches of the 1.5 inch needle length will not be inserted through the skin of the patient). It should be understood that knowledge of the angle needed to be used to reached the desired vessel is important for both needle guide and needle anchor features.

Figures 3A, 3B, 3C, 3D:
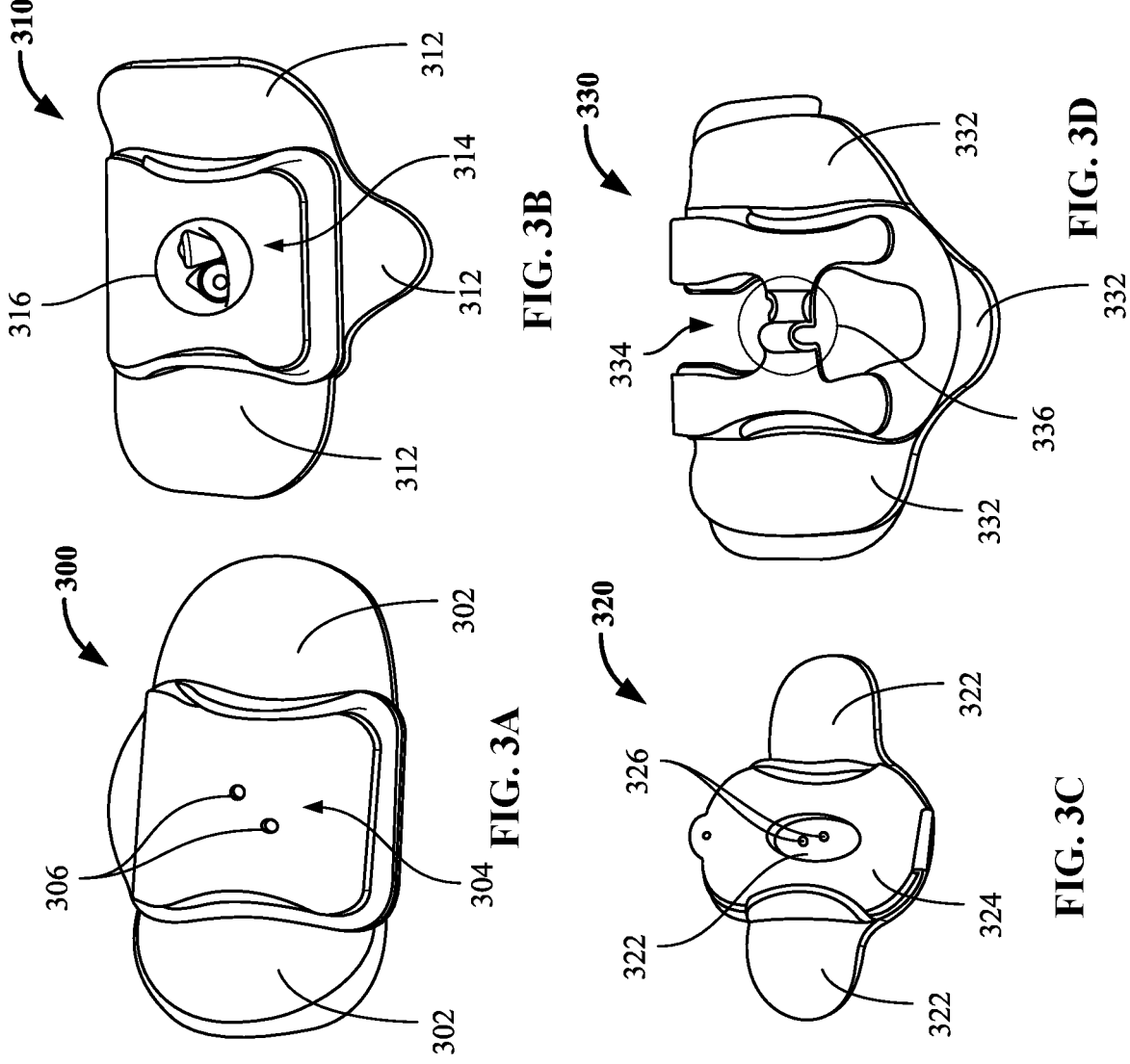
FIG. 3A is a top view illustrating an example of a fold-over external needle guide with two needle markers.
FIG. 3B is a top view illustrating an example of a fold-over external needle guide with two needle slots.
FIG. 3C is a top view illustrating an example of a fold-over external needle guide with two needle markers.
FIG. 3D is a top view illustrating an example of a fold-over external needle guide with two needle notches.

FIGS. 3A-3D illustrate various implementations of fold-over needle guide portions providing a guide for insertion of needles/cannulas into a patient. FIG. 3A is a top view illustrating an example of a fold-over external needle guide with two needle markers. Referring to FIG. 3A, a fold-over external needle guide 300 (which is shown in closed position) includes a skin contact portion 302 and a needle guide portion 304. In the illustrated implementation, the needle guide portion 304 includes two needle markers 306. When the external needle guide 300 is in the closed position (e.g., via a hinge not shown in this view), needles can be placed through the two needle markers 306 and into a vessel of a patient. Since, in this case, the needle markers 306 do not control the angles at which the needles are inserted, the external needle guide 300 is most suitable when there is a (relatively) large amount of room for error for the angles at which the needles are inserted or the needles can be placed into the vessel of the patient straight down (i.e., perpendicular to the skin of the patient). The skin contact portion 302 may also include adhesive (e.g., similar to the adhesive tabs found on an adhesive bandage) for attaching the external needle guide 300 to the skin of the patient.

FIG. 3B is a top view illustrating an example of a fold-over external needle guide with two needle slots. As used herein, a "needle slot" refers to a tube-like structure (three dimensional) in which a needle can be inserted that controls the angle relative to the surface of the skin in which the needle is inserted into the vessel of the patient (and may also prevent the needle from being inserted past a predetermined depth). Furthermore, a needle slot may be formed within material of the needle guide portion (e.g., such that the needle slot does not protrude from the material of the needle guide portion). Referring to FIG. 3B, a fold-over external needle guide 310 (which is shown in closed position) includes a skin contact portion 312 and a needle guide portion 314. In the illustrated implementation, the needle guide portion 314 includes two needle slots 316. When the external needle guide 310 is in the closed position (e.g., via a hinge not shown in this view), needles can be placed through the two needle slots 316 and into a vessel of a patient. The angles at which the needles can be inserted into the skin of the patient are controlled by internal walls of the two needle slots 316. Indeed, not only are the angles controlled, but the depth at which the needles can be inserted may also be controlled by way of a tapered structure of the two needle slots 316 or by way of a catch structure of the two needle slots 316. Therefore, by using an external needle guide 310 with needle slots 316, a patient and/or another person can insert needles without worry of recirculation and/or damage to the vessel of the patient. The skin contact portion 312 may also include adhesive for attaching the external needle guide 300 to the skin of the patient.

FIG. 3C is a top view illustrating an example of a fold-over external needle guide with two needle markers. Referring to FIG. 3C, a fold-over external needle guide 320 (which is shown in closed position) includes a skin contact portion 322 and a needle guide portion 324. In the illustrated implementation, the needle guide portion 324 includes two needle markers 326. The skin contact portion 322 may also include adhesive (e.g., similar to the adhesive tabs found on an adhesive bandage). In this embodiment, because the needle guide portion 324 also contacts the skin of the patient, the needle guide portion 324 may also include an adhesive to contact the skin of the patient. The needle guide portion 324 can also include a place for the patient/other person to secure/anchor a body of a needle during dialysis. This can be especially useful if the patient is receiving dialysis in a place in which people are moving around and likely to (accidentally) dislodge the needles from the patient.

When the external needle guide 320 is in the closed position (via a hinge not shown in this view), needles can be placed through the two needle markers 326 and into a vessel of a patient. Since the needle markers 326 do not control the angles at which the needles are inserted, this example may be used when there is a (relatively) large amount of room for error for the angles at which the needles are inserted or the needles can be placed into the vessel of the patient straight down (i.e., perpendicular to the skin of the patient).

FIG. 3D is a top view illustrating an example of a fold over external needle guide with two needle notches. As used herein, a "needle notch" refers to an indentation (three dimensional) formed along an edge of the material of the needle guide portion that is made to guide a needle into a vessel of the patient at a predetermined angle (and may also prevent the needle from being inserted past a predetermined depth). Referring to FIG. 3D, a fold over external needle guide 330 includes a skin contact portion 332 and a needle guide portion 334. The needle guide portion 334 includes two needle notches 336. In the closed position, a needle may be placed through each of the two needle notches 336, through the skin of the patient, and into a vessel of the patient. Because the needle notches 336 are open towards the skin of the patient, when needles are inserted through needle notches 336, a maximum angle at which the needles are inserted through the skin of the patient is provided. Although a minimum angle is not provided (e.g., because the needle notches 336 do not include material between a needle and the skin of the patient), a patient/other person inserting the needles can use the top of the needle notches 336 as a guide in placing the needle into the vessel of the patient. Furthermore, after the needle is inserted into the vessel of the patient, the needles can be secured (e.g., via tape) to the side of the external needle guide 330 and/or skin of the patient to prevent the needles from being (accidentally) dislodged during dialysis. The depth at which the needles can be inserted may also be controlled by way of a tapered structure of the two needle notches 336 or by way of a catch structure of the two needle notches 336. The angle and/or depth control allow a patient and/or another person to insert needles without worry of recirculation and/or damage to the vessel of the patient. The skin contact portion 332 may also include adhesive for attaching the external needle guide 300 to the skin of the patient.

Figure 4A:
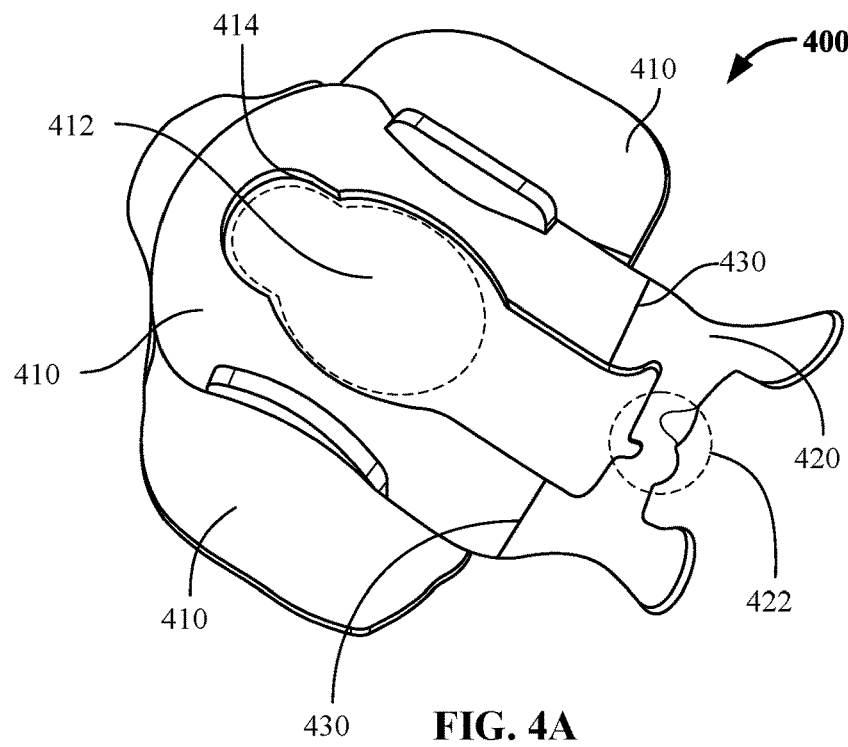
FIG. 4A is an angled view illustrating an example of an external needle guide in an open position.
Figure 4B:
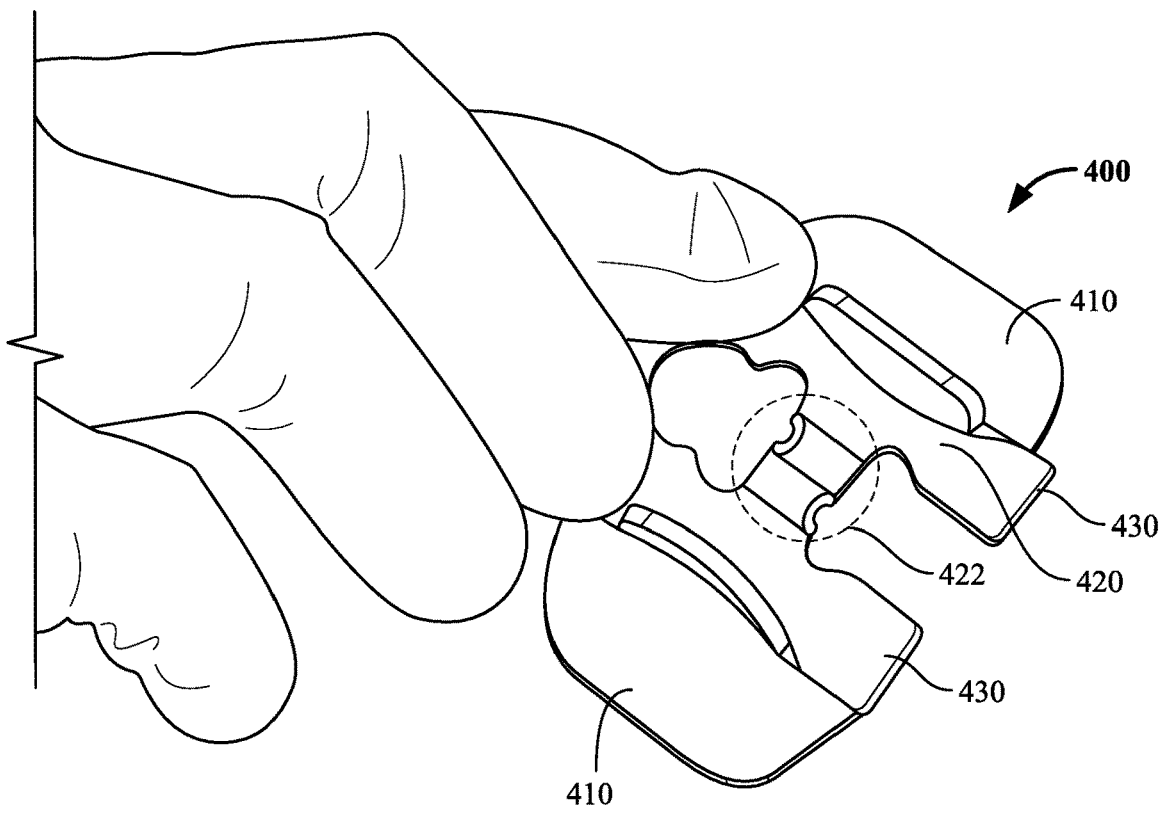
FIG. 4B is an angled view illustrating an example of an external needle guide in a closed position.

FIG. 4A is an angled view illustrating an example of the fold-over external needle guide of FIG. 3D in an open position. The skin contact portion 410 of the external needle guide 400 includes an opening 412 in a central region 414. The opening 412 has a size that is large enough for a finger (e.g., of a patient and/or another person) to pass through to feel for a palpable indication of the vessel of the patient. Once the palpable indication of the location of the vessel is found beneath the skin of the patient, the external needle guide 400 is secured to the skin of the patient via the skin contact portion 410. Once secured to the skin of the patient, the external needle guide 400 is moved to the closed position (as can be seen in FIGS. 3D and 4B) via the hinge 430. The hinge 430 may be any suitable hinge including, but not limited to, a spring hinge, barrel hinge, pivot hinge, mortise hinge, case hinge, piano hinge, concealed hinge, butterfly hinge, flag hinge, strap hinge, H hinge, HL hinge, self-closing hinge, counterflap hinge, flush hinge, coach hinge, rising butt hinge, double action spring hinge, double action non-spring hinge, tee hinge, friction hinge, security hinge, cranked hinge, lift-off hinge, or any other hinge suitable for moving the needle guide portion 420 between the open position and the closed position. Furthermore, the hinge may be a living hinge. A "living hinge" refers to a thin, flexible hinge made from the same material as the two rigid pieces it connects. Typically, during manufacturing, a living hinge is thinned or cut out to allow the rigid pieces to bend along the line of the hinge.

FIG. 4B is an angled view illustrating an example of the external needle guide of FIG. 3D in a closed position. As can be seen, once secured to the skin of the patient, the external needle guide 400 is moved to the closed position via the hinge 430. Once moved to the closed position, a patient/other person may insert the needles into the vessel of the patient via the two needle notches 422.

Figure 5A:
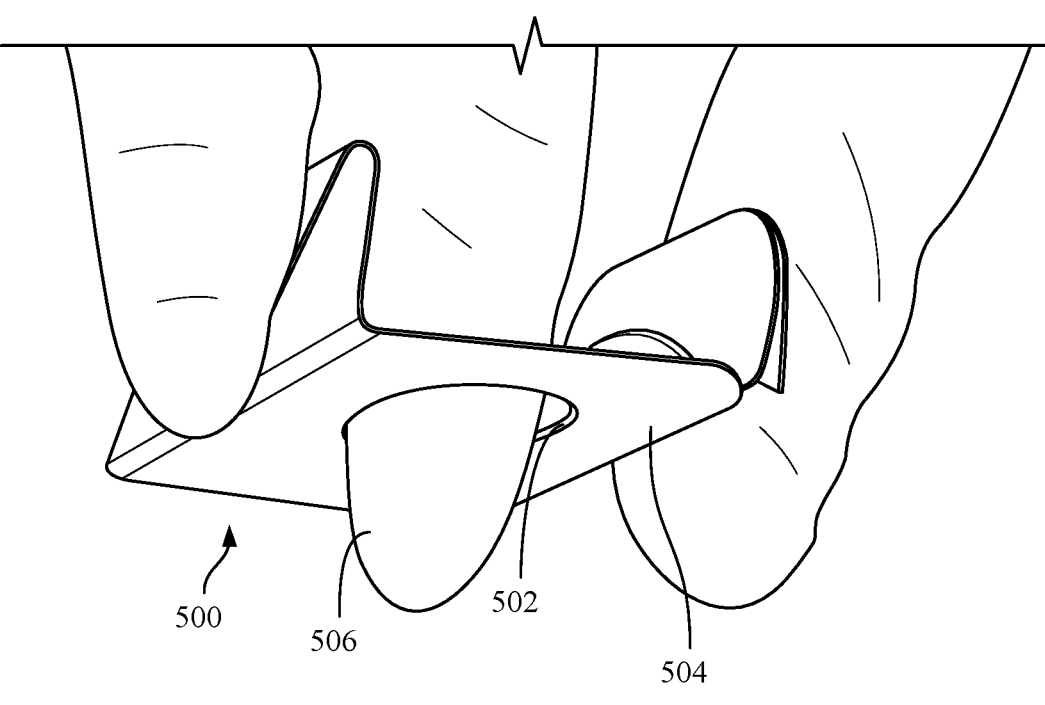
FIGS. 5A-5H illustrate a method of using an example external needle guide.

FIGS. 5A-5H illustrate a method of using an example external needle guide of FIG. 3B. FIG. 5A illustrates a patient and/or another person placing their finger through the skin contact portion of an external needle guide. The external needle guide 500 includes an opening 502 in the skin contact portion 504 that is large enough to enable a finger 506 (e.g., of the patient and/or another person) to pass therethrough.

Figure 5B:
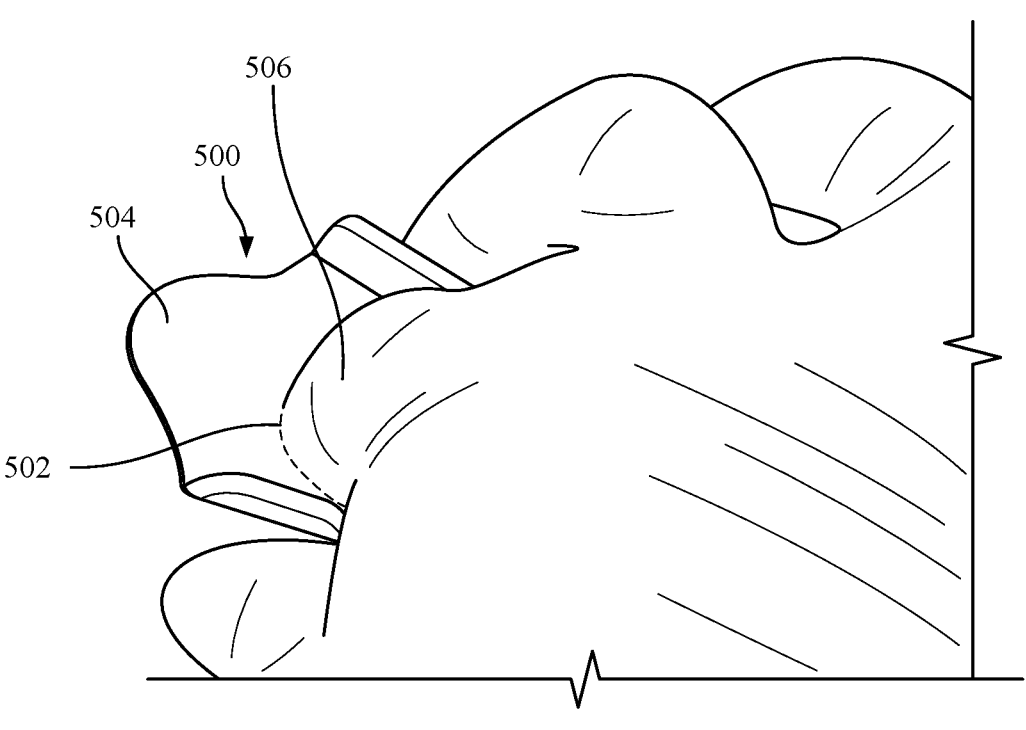

FIG. 5B illustrates a patient and/or another person feeling for a palpable indication of a location of a vessel through the skin contact portion of an external needle guide. As can be seen, a patient and/or another person has placed their finger 506 within the opening 502 of the skin contact portion 504 in order to feel for a palpable indication of the vessel of the patient. The palpable indication may be the vessel itself, a specific palpable feature of the user that is at or near the vessel (e.g., a bone, a scar, a muscle, a tendon, or any other feature that the user knows is a certain distance and/or direction from the vessel), or even a vascular port that has been placed around the vessel (and that includes a palpable feature). The user can then position the external needle guide 500 in the appropriate position so that a needle(s) can be inserted into the vessel.

Figure 5C:
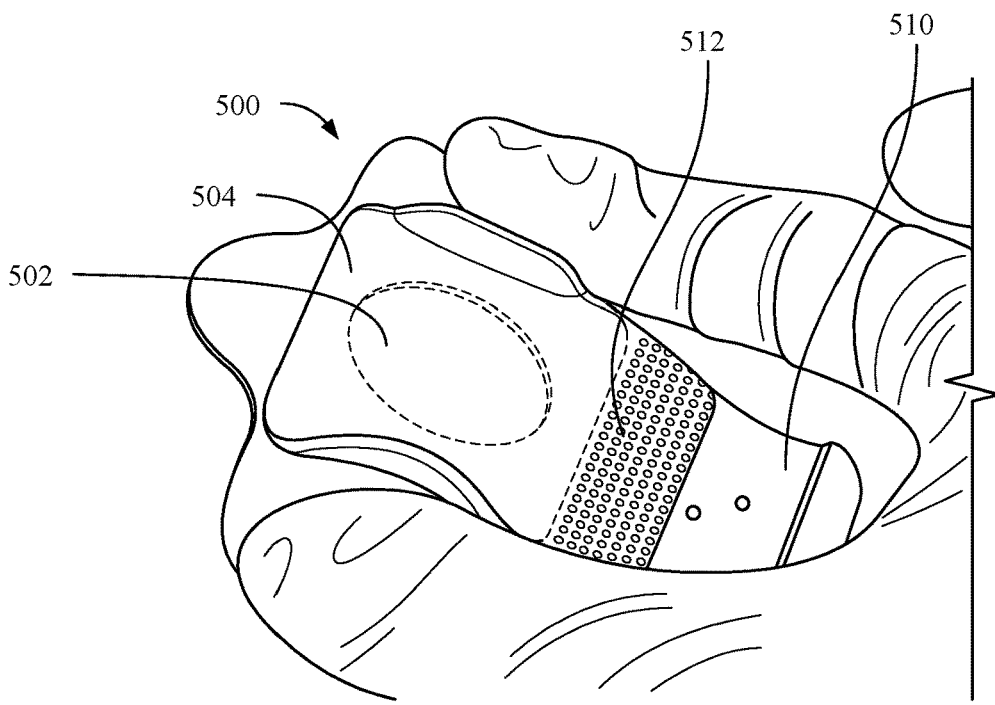

FIG. 5C illustrates a patient and/or another person securing the external needle guide to a position on the skin of a patient. After the patient and/or another person finds the palpable indication of the vessel and positions the external needle guide 500 in the appropriate position so that a needle(s) can be inserted into the vessel, the patient and/or another person secures the skin contract portion 504 to the skin of the patient. In this example, the skin contact portion 504 is attached to the skin of the patient with an adhesive on the skin contact portion 504. However, in some examples, the external needle guide 500 may be secured into position with a mechanical attachment to the skin of the patient. As a specific example, the skin contact portion 504 may be configured to attach to a vascular port underneath the skin of the patient. In this example, the skin contact portion 504 may also include a local anesthetic to prevent any discomfort from the mechanical attachment (e.g., pinching of the skin). In other examples, the external needle guide 500 may be secured into position with a magnetic attachment. For instance, a vascular port or graft underneath the skin of the patient may have ferromagnetic material contained within and the external needle guide 500 may contain a magnetic portion that positions the external needle guide 500 (due to the ferromagnetic material in the vascular port underneath the skin of the patient) into the correct position for needle(s) insertion into the vessel.

Figure 5D:
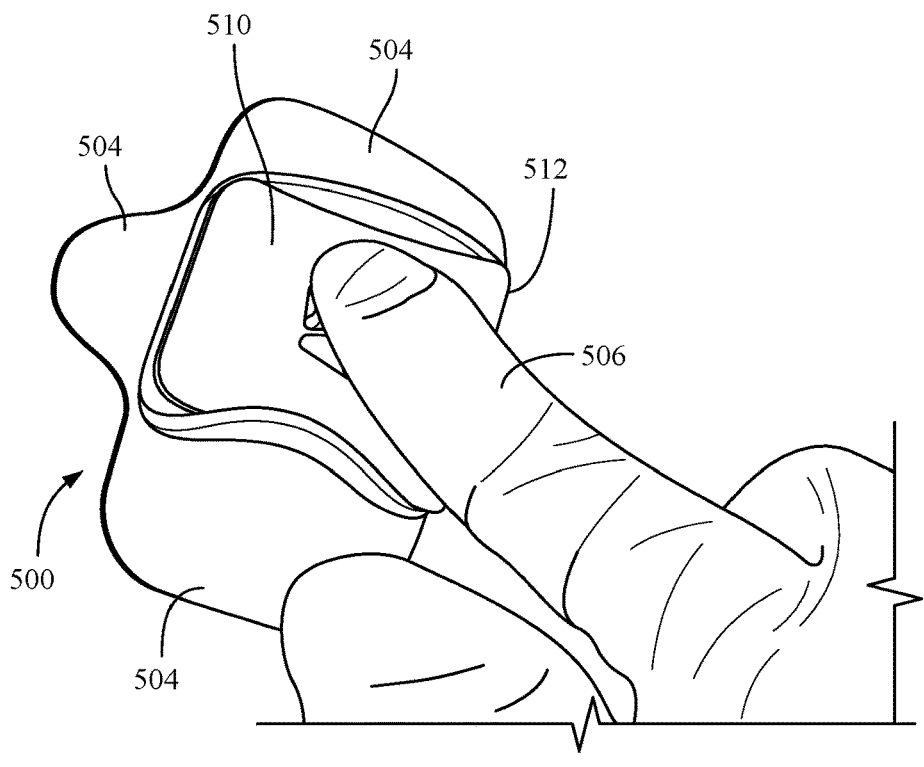

FIG. 5D illustrates a patient and/or another person positioning the needle guide portion over the skin contact portion of an external needle guide. After the patient and/or another person secures the skin contact portion 504 to the skin of the patient, the patient and/or another person can move the needle guide portion 510 over the opening 502 in the skin contact portion 504 to a closed position via the hinge 512 of the fold-over external needle guide 500. In some cases, the skin contact portion 504 and the needle guide portion 510 can attach to each other via a snap fit mechanism, latch, or any other design that enables the skin contact portion 504 and the needle guide portion 510 to securely attach to one another.

Figure 5E:
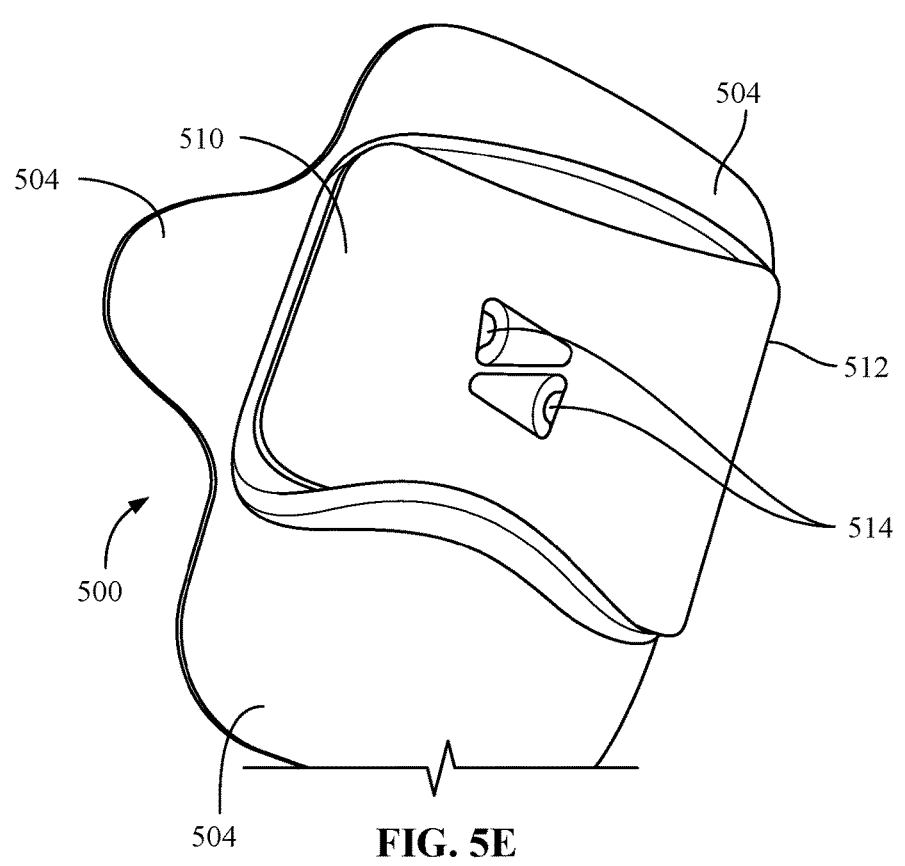

FIG. 5E illustrates the external needle guide in position for needle insertion on the skin of a patient. After the patient and/or another person has moved the needle guide portion 510 over the opening 502 in the skin contact portion 504 to a closed position via the hinge 512 of the fold-over external needle guide 500, the external needle guide 500 is ready for needle insertion. As can be seen in this example, the needle guide portion 510 of the external needle guide 500 includes two needle slots 514. The needle slots 514 are set at a predetermined angle relative to the skin of the patient, which, for example, can prevent recirculation of the blood of the patient during dialysis. Furthermore, the needle slots 514 may also include a tapered structure or a catch structure to control the depth at which the needles can be inserted into the needle slots 514, which prevents damage to the vessel and surrounding tissue.

Figure 5F:
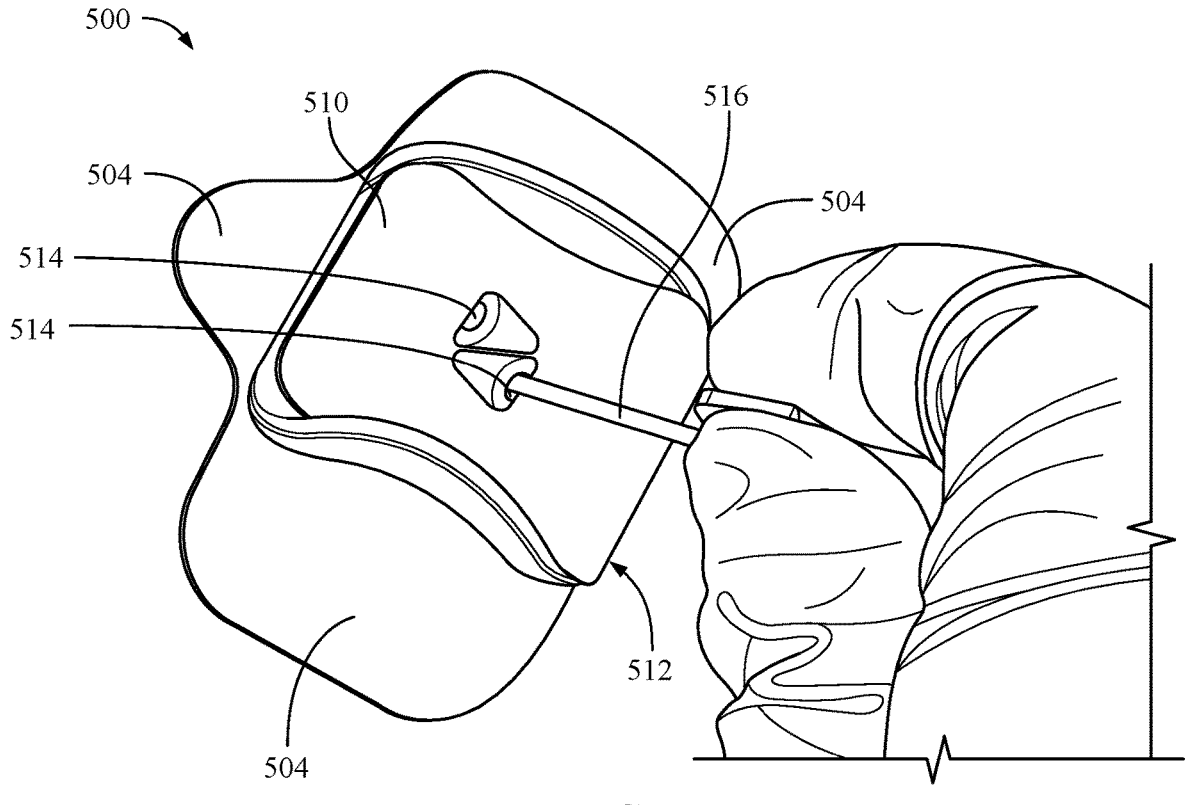
Figure 5G:
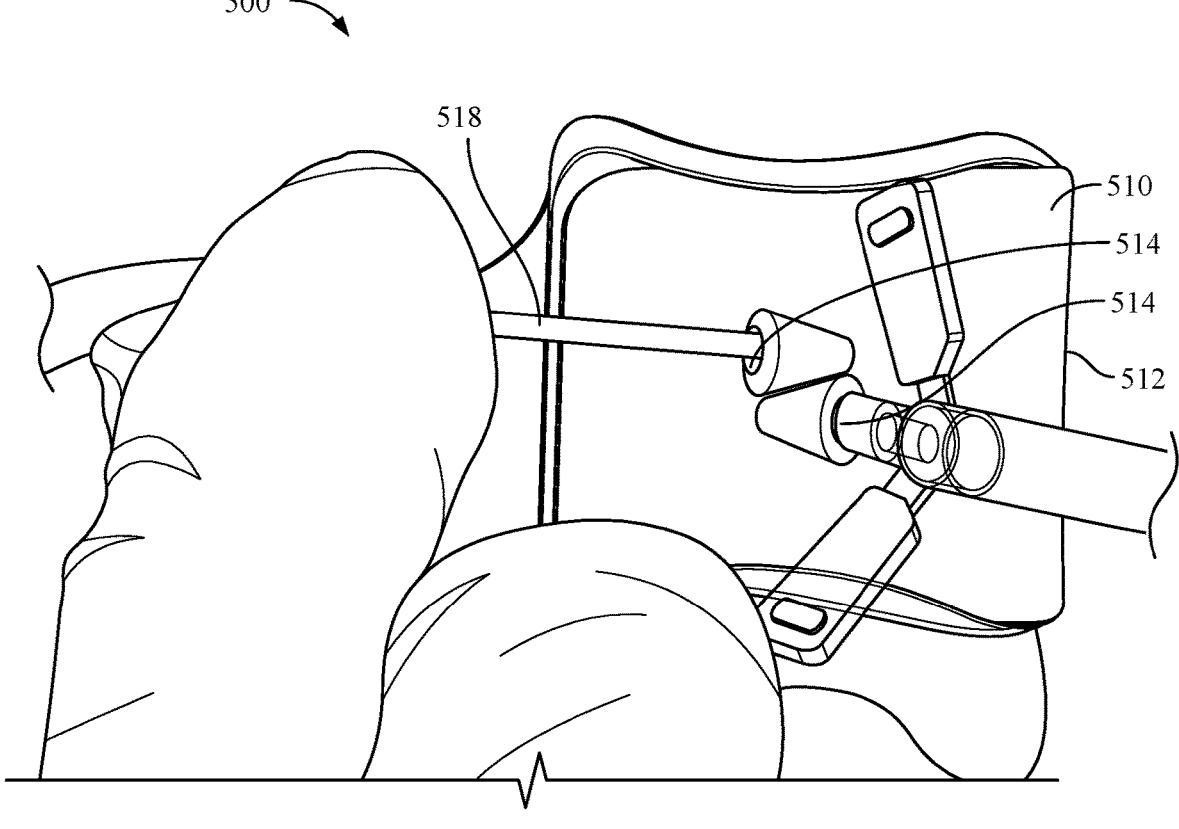

FIG. 5F illustrates a patient (or other person) inserting a needle into a needle guide slot of an external needle guide. FIG. 5G illustrates a patient (or other person) inserting a needle into a second needle guide slot of an external needle guide. The tapered and/or catch structure of the needle slots 514 prevent the needles 516, 518 from being inserted into the vessel further than intended and the predetermined angle relative to the skin of the patient ensures that the tips of the needles 516, 518 are spaced far enough from one another to prevent recirculation of the patient's blood. It should be understood that the needles 516, 518 are a predetermined length; however, the tapered and/or catch structure of the needle slots 514 can be specific to each patient (e.g., based on the depth of the vessel from the skin of the patient) and the length of needle that will be used in the vessel of that patient.

Figure 5H:
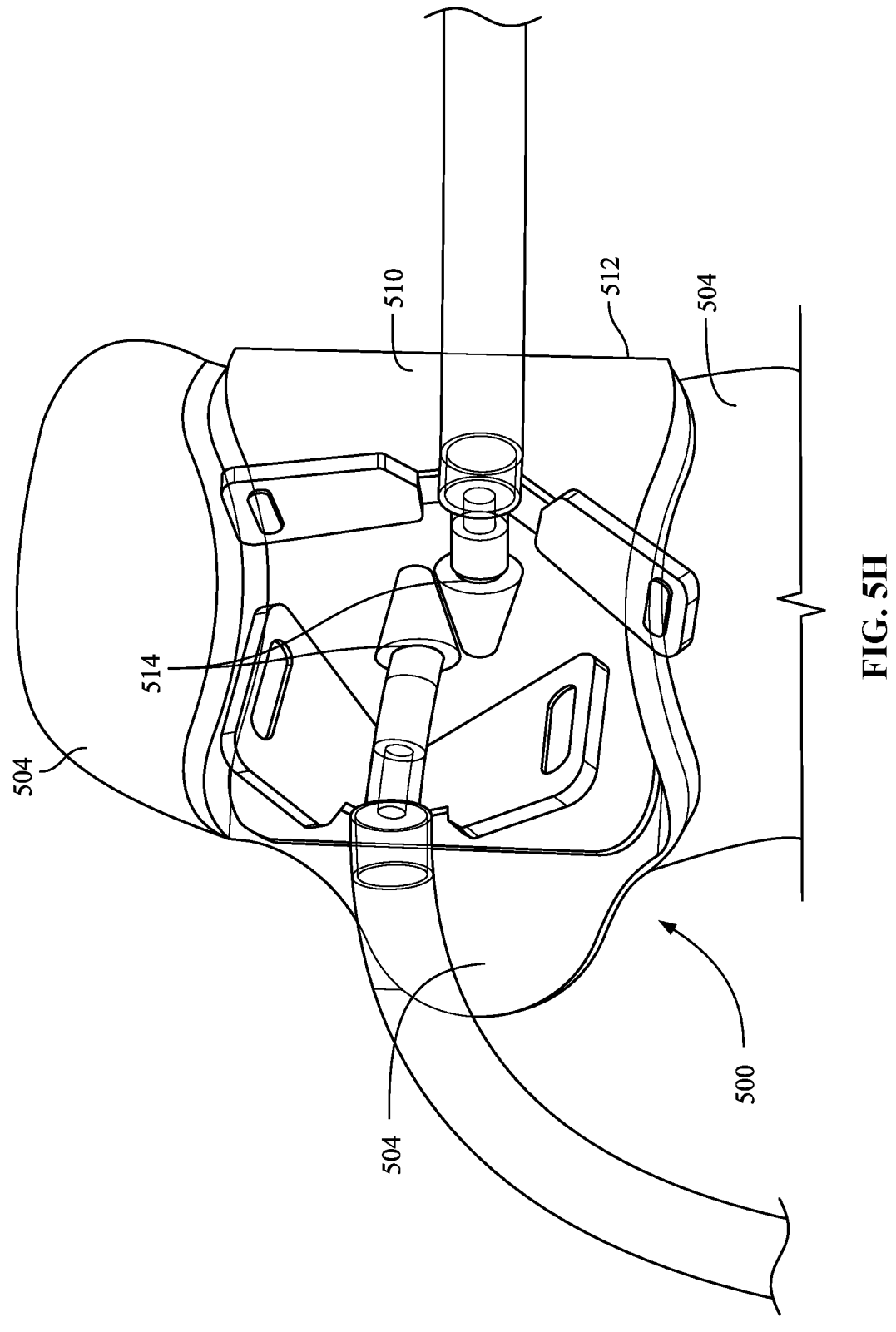

FIG. 5H illustrates an external needle guide with two needles inserted into a patient. The needles 516, 518 have been inserted through the skin of the patient and into the vessel. The external needle guide 500 has been used (as explained above) to insert the needles 516, 518 into the vessel without damage to the vessel due to the predetermined angle of the needle slots 514 and the tapered and/or catch structure of the needle slots 514. Furthermore, because of the predetermined angle of the needle slots 514 and the corresponding length of the needles 516, 518, the tips of the needles are spaced within the vessel so that no recirculation of the blood occurs.

Advantageously, all of the actions carried out by a patient and/or another person described in FIGS. 5A-5H, including being able to position and secure the external needle guide as well as to cannulate the vessel, may be accomplished with one hand. As explained above, this ensures that a patient can successfully cannulate themselves without the help of another person.

Figure 6A:
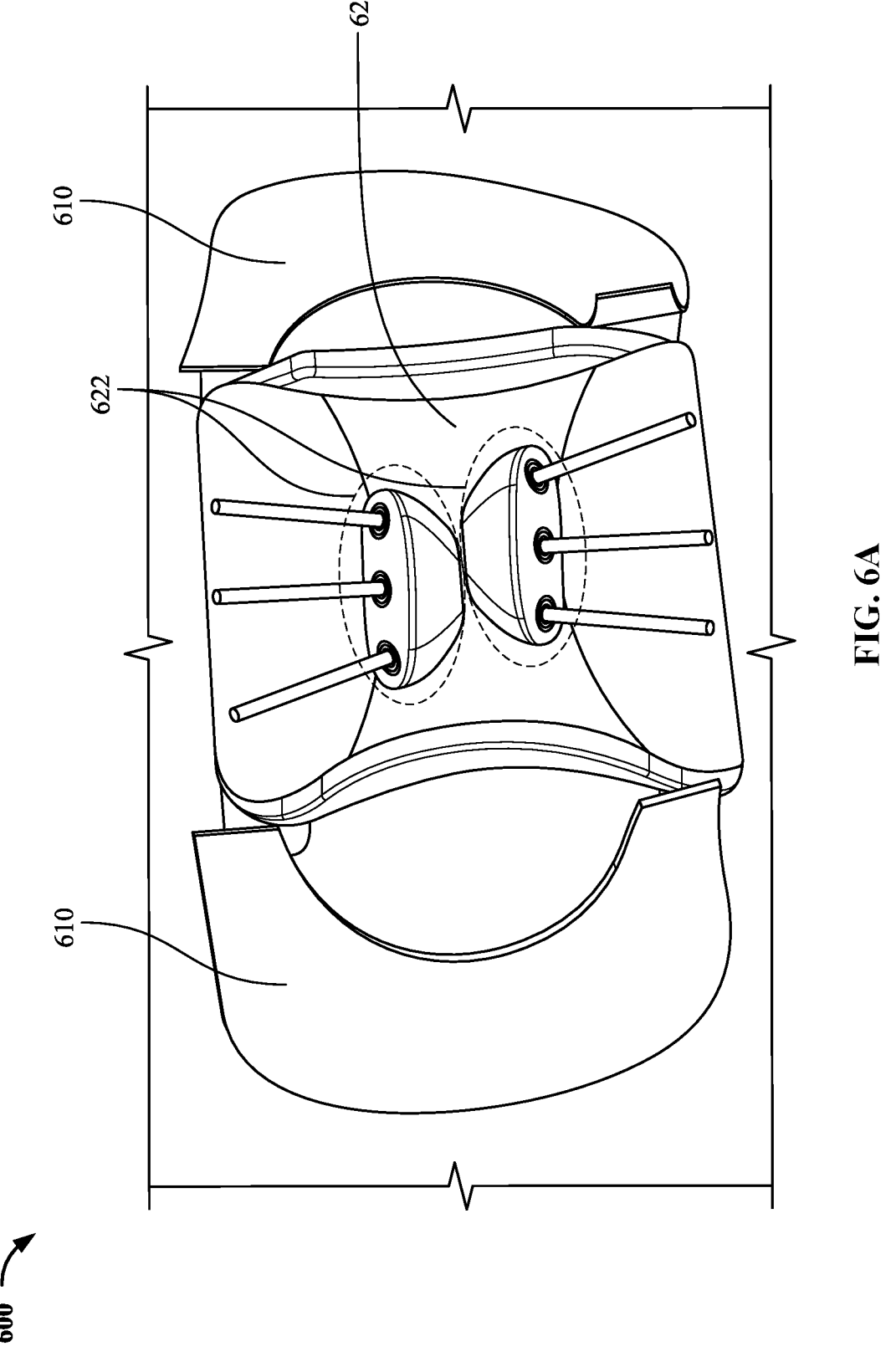
FIG. 6A illustrates an external needle guide with a plurality of needle slots.

FIG. 6A illustrates an external needle guide with a plurality of needle slots. The external needle guide 600 includes a skin contact portion 610 and a needle guide portion 620. In this example, the skin contact portion 610 includes an opening in a central region (e.g., not shown in this Figure due to the fold-over design of this implementation being in the closed position) that a patient and/or another person can use to feel (e.g., via a finger) for a palpable indication of a vessel of the patient. In this example, the needle guide portion 620 includes a plurality of needle slots 622 to provide multiple options for inserting a needle. Although six needle slots are shown, more or fewer can be provided. In addition, although the plurality of needle slots is shown both as slots and on a fold-over type of design, the plurality of needle slots may be in the form of markers, slots, apertures, or notches. In addition, the type of design can be of any type described herein and not just the fold-over type.

Figure 6B:
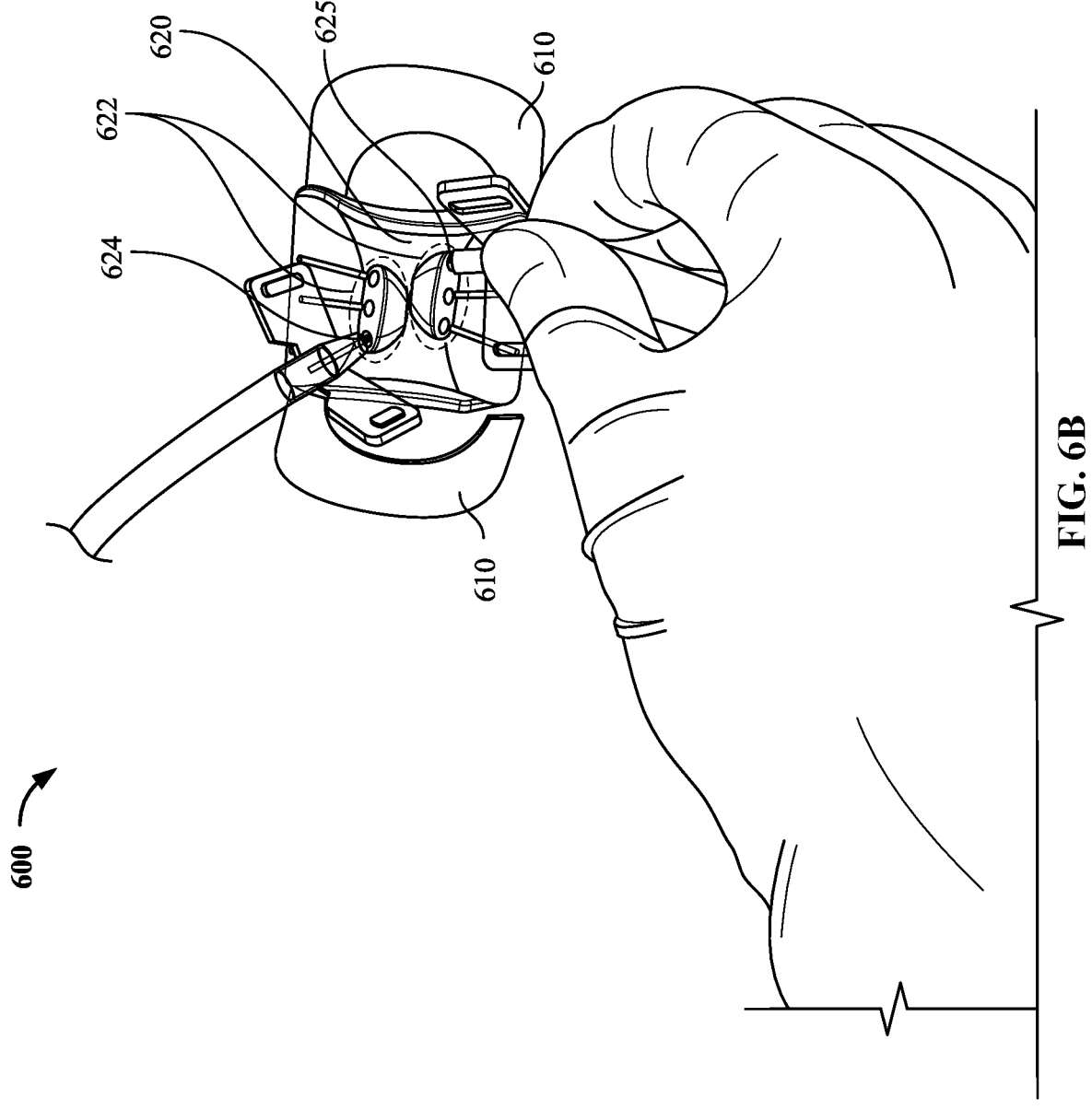
FIG. 6B illustrates the external needle guide of FIG. 6A in use with needles.

FIG. 6B illustrates the external needle guide of FIG. 6A in use with needles. In the illustrated example, the external needle guide 600 has two needles 624, 625 in two corresponding needle slots of the plurality of needle slots 622.

Depending upon which needle slot of the plurality of needle slots 622 the needles 624, 625 are inserted through, the needles 624, 625 may have a different entrance point (i.e., puncture location) on the skin of the patient and in a vessel of the patient. The ability to change which slots to use can help minimize damage to a particular region of a vessel over time.

Figure 6C:
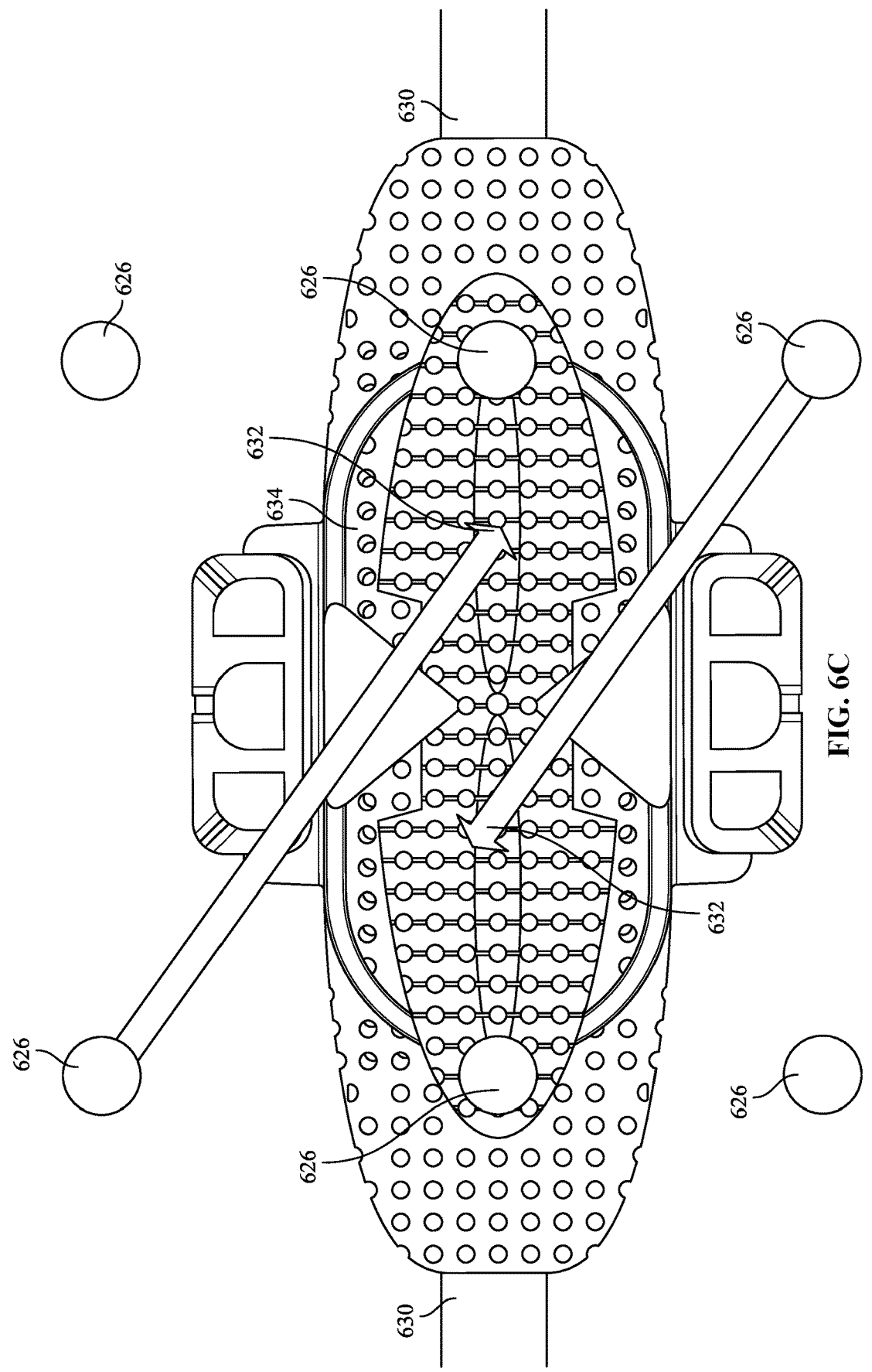
FIG. 6C illustrates paths of needles into a vessel encompassed by an internal vascular port.

FIG. 6C illustrates paths of needles into a vessel encompassed by an internal vascular port. As can be seen, the entrance 626 for each needle slot 622 are located at various positions relative to the vessel 630 of the patient. When needles 624, 625 are placed into the needle slots 622 as shown in FIG. 6B, the path of the needles 624, 625 puncture different locations on the skin of the patient and puncture different locations 632 within the vessel 630 than if different corresponding needle slots 622 were utilized to insert the needles 624, 625 into the vessel of the patient. This allows the skin of the patient and puncture locations 632 within the vessel 630 to heal in between each treatment session. For example, if a patient needs dialysis three times per week, a plurality of needle slots 622 can be included so that for each dialysis session, a different puncture location 632 within the vessel 630 and a different puncture location on the skin of the patient is punctured in each session, giving each respective puncture location on the skin of the patient and location 632 within the vessel 630 a week to heal (as opposed to approximately two days to heal if the same puncture location on the skin of the patient and same puncture location 632 within the vessel are used in each treatment session). It should be understood that, in some cases, the vessel 630 can be encompassed by a vascular port 634.

Figure 7A:
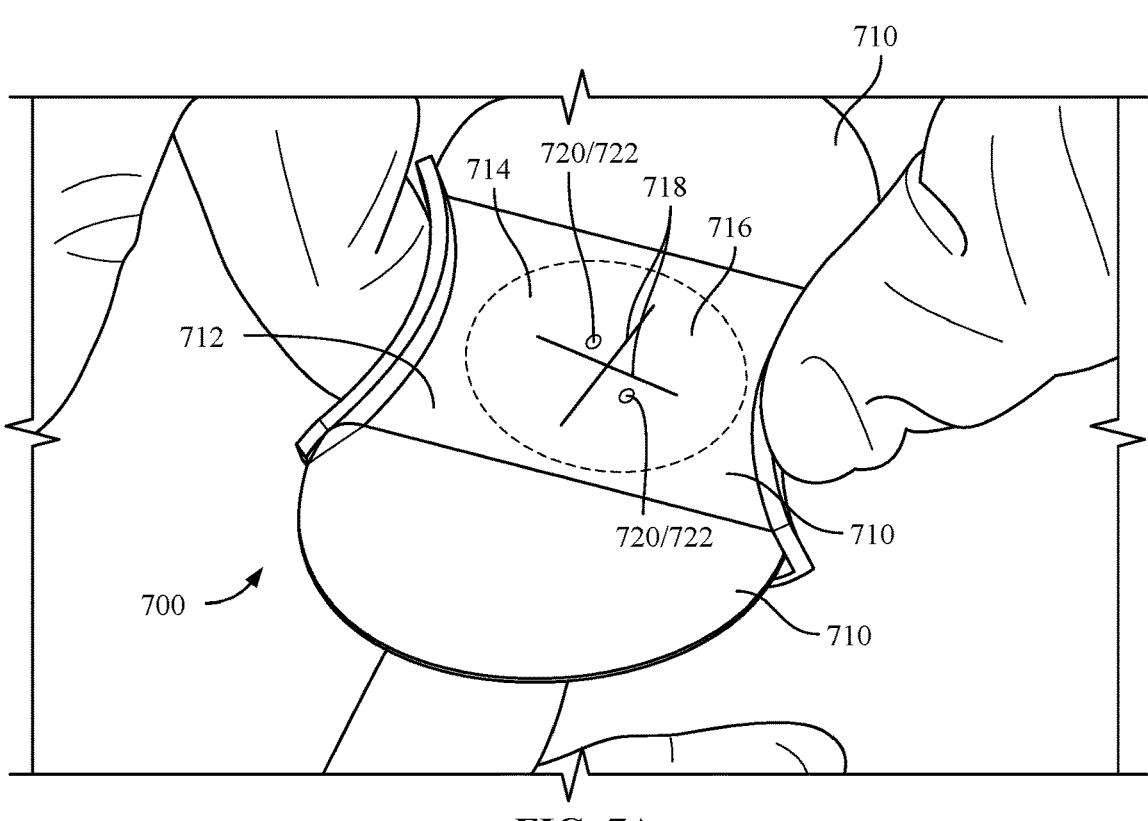
FIG. 7A illustrates an external needle guide having two needle markers on a flexible barrier of the skin contact portion.

FIG. 7A illustrates an external needle guide having two needle markers on a flexible barrier of the skin contact portion. The external needle guide 700 includes a skin contact portion 710 and a needle guide portion 720. The skin contact portion 710 includes a central region 712 having an opening 714. Covering/disposed over the opening 714 is a soft barrier 716. In some cases, the soft barrier 716 may be made of any material that is deformable through touch of a patient/other person's finger. Examples of material that is deformable through touch of a patient/other person's finger may include, but are not limited to, polymer membranes such as latex, polyurethane cellophane, and the like or even wax. In some cases, the soft barrier 716 may include slits 718; in these cases, the soft barrier 716 may be made of a rigid material. Examples of rigid material may include, but are not limited to, composite materials and tough plastics such as polyethylene terephthalate, polyethylene, polyvinyl chloride, polypropylene, polylactic acid, polycarbonate, acrylic, acetal, acrylonitrile butadiene styrene, and the like. Furthermore, when the soft barrier 716 is made of rigid materials, living hinges may be incorporated to allow a finger of a patient and/or another person to move through the opening 714 (e.g., as illustrated in FIG. 7B).

Needle markers 722 are included and serve as the needle guide portion 720. The needle markers 722 are used for placement of two needles into a vessel of the patient. In some cases, the needle markers 722 may be needle slots, needle notches, and/or needle apertures.

Figure 7B:
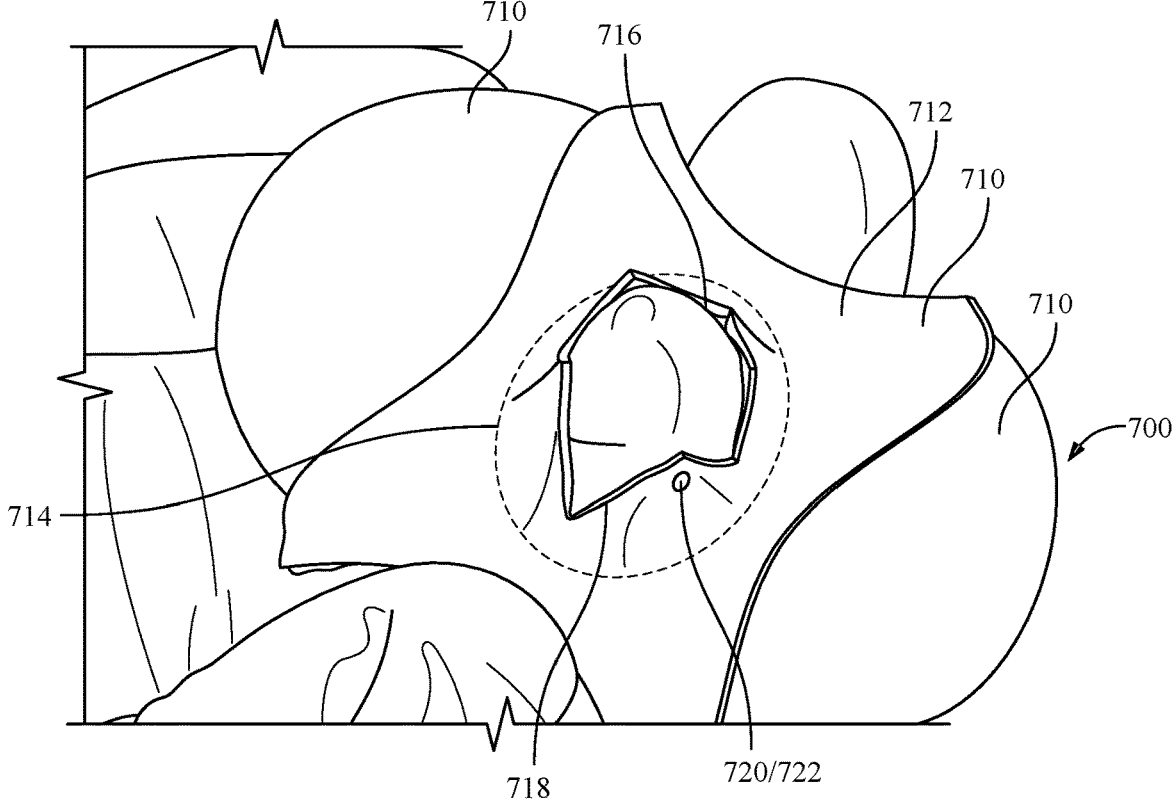
FIG. 7B illustrates a patient and/or other person placing their finger through a slit in the skin contact portion of an external needle guide.

FIG. 7B illustrates a user placing their finger through a slit in the skin contact portion of an external needle guide. As can be seen in FIG. 7B, the slits 718 allow for a patient and/or another person to place their finger through the soft barrier 716 of the opening 714. It should be understood that in cases where the soft barrier 716 includes slits 718, the material may be made of deformable or rigid material.

Figure 7C:
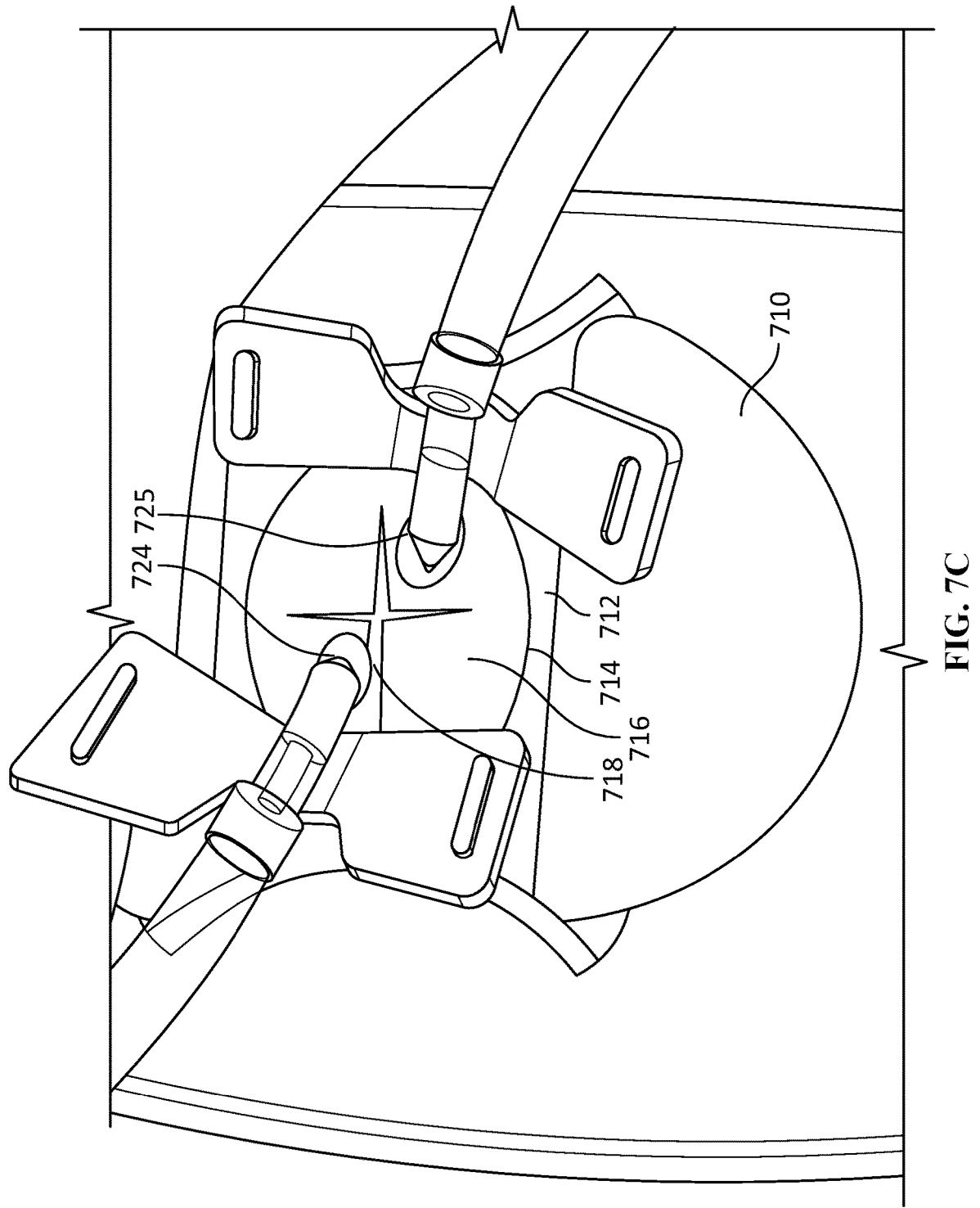
FIG. 7C illustrates an external needle guide with two needles inserted into a patient.

FIG. 7C illustrates an external needle guide with two needles inserted into a vessel of patient. The needle markers 722 can be used to insert needles 724, 725 into the vessel of the patient. As explained above, in some cases, the needle markers 722 may include one or more needle slots, needle notches, and/or needle apertures.

Figure 8:
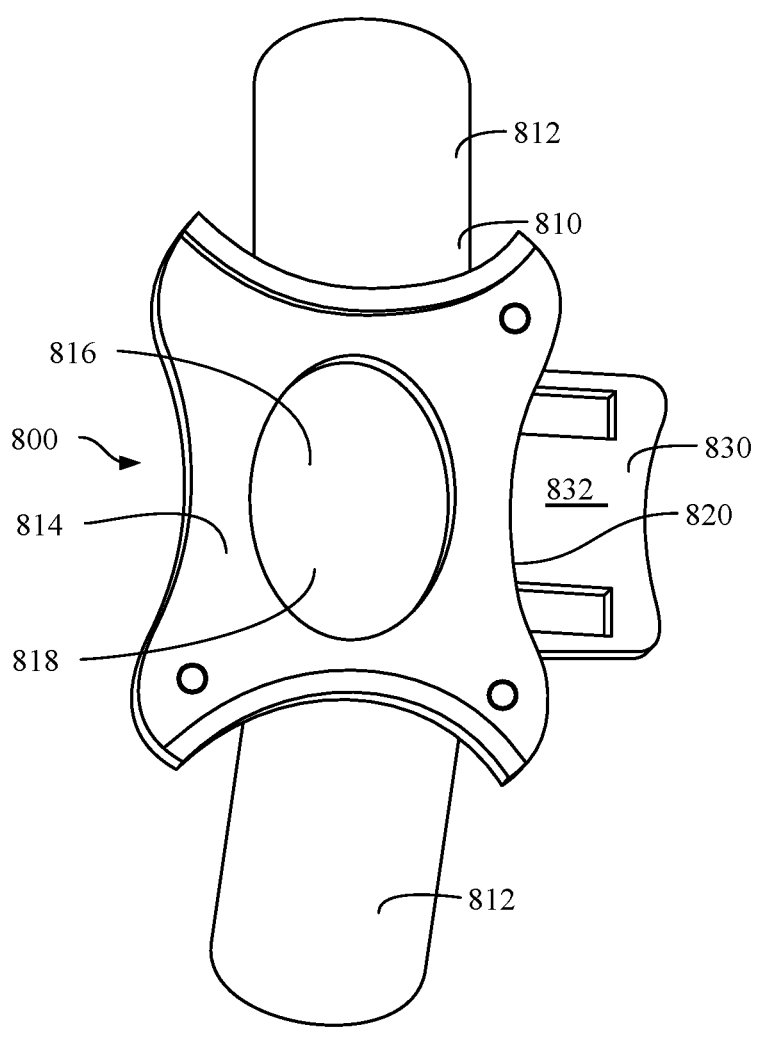
FIG. 8 illustrates an external needle guide with a needle guide slide.

FIG. 8 illustrates an external needle guide with a needle guide slide. The external needle guide 800 includes a skin contact portion 810 and a needle guide portion 830. The skin contact portion includes adhesive flaps 812 extending from a central region 814. The central region 814 includes an opening 816. Covering the opening 816 is a soft barrier 818. The skin contact portion 810 further includes a guide slot 820 that is used to receive a needle guide slide 832 of the needle guide portion 830.

The guide slot 820 enables the needle guide slide 832 to be positioned over the opening 816. In other words, the patient and/or another person can use the opening 816 to feel for a palpable indication of a vessel of the patient. As can be seen in FIG. 8, the needle guide slide 832 is in the palpable position so that the patient and/or another person can feel (e.g., via the opening 816) for the palpable indication of a vessel of the patient. Upon finding the palpable indication of a vessel of the patient and securing the external needle guide 800 to the skin of the patient, the patient and/or another person can move the needle guide slide 832 in a needle insertion position for inserting a needle(s) into the vessel of the patient. In some cases, the needle guide slide 832 can move from the palpable position to the needle insertion position via a track-like mechanism within the guide slot 820. In some cases, the guide slot 820 may include a catch-like mechanism to secure the needle guide slide 832 into the needle insertion position so there is no movement of the needle guide slide 832 during needle insertion. In some cases, the guide slot 820 may include a catch-like mechanism to secure the needle guide slide 832 in the palpable position so there is no movement of the needle guide slide 832 when the patient and/or another person is feeling for the palpable indication of the vessel of the patient. It should be understood that the needle guide slide 832 may include one or more needle markers, needle slots, needle notches, and/or needle apertures.

Figure 9A:
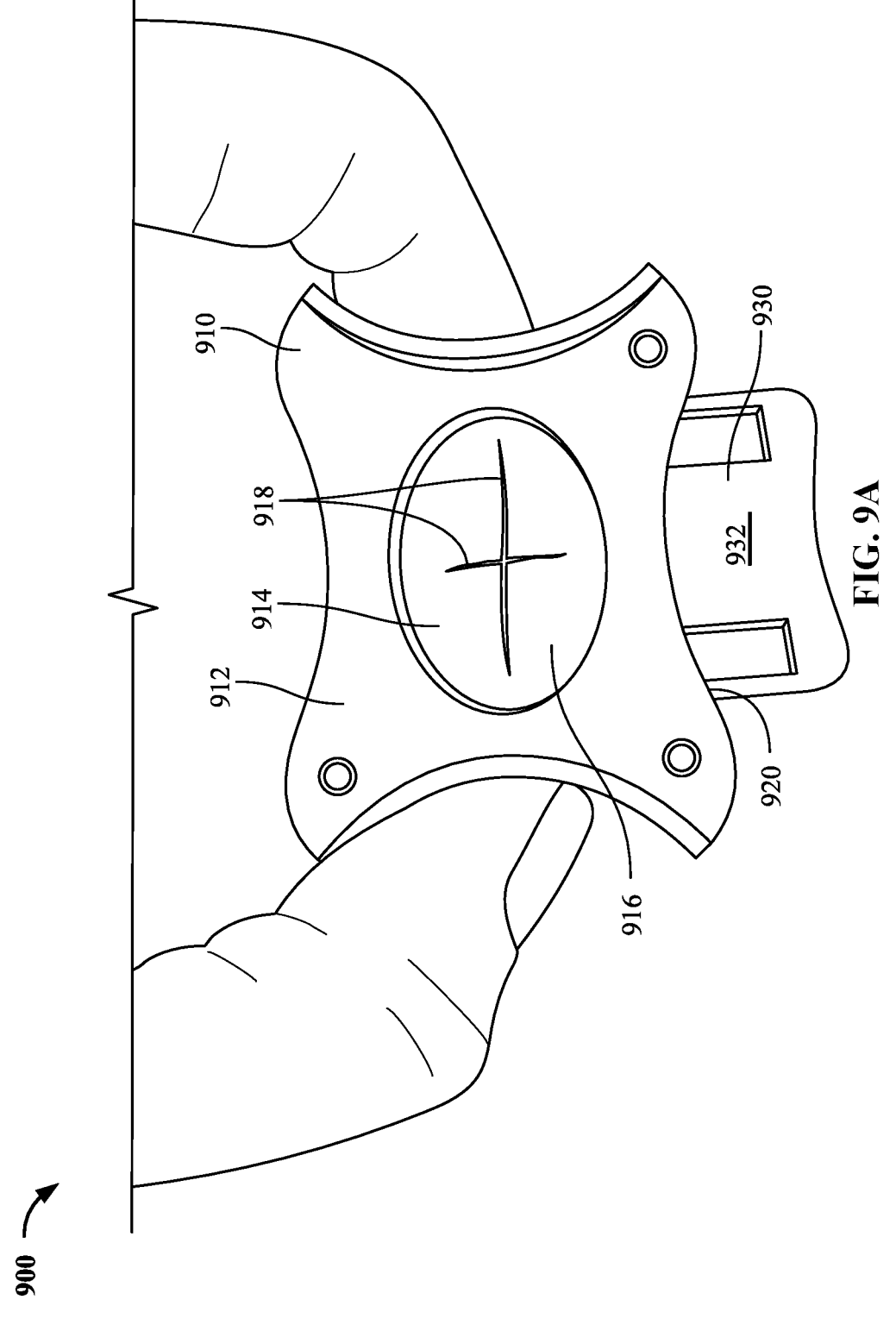
FIG. 9A illustrates an external needle guide with a needle guide slide in the palpable position.

FIG. 9A illustrates an external needle guide with a needle guide slide in the palpable position. The external needle guide 900 includes a skin contact portion 910 and a needle guide portion 930. The skin contact portion includes a central region 912 having an opening 914. In this case, the central region 912 is made of a rigid material (e.g., similar to the rigid material described in FIG. 1A). Covering the opening 914 is a soft barrier 916. In some cases, the soft barrier 916 may be made of any material that is deformable through touch of a patient/other person's finger. In some cases, the soft barrier 916 may include slits 918 (e.g., similar to slits 718 of FIG. 7A-7C); in these cases, the soft barrier 916 may be made of a rigid material or deformable material. The skin contact portion 910 further includes a guide slot 920 that is used to receive a needle guide slide 932 of the needle guide portion 930.

The patient and/or another person can use the opening 914 to feel for a palpable indication of a vessel of the patient. As can be seen in FIG. 9A, the needle guide slide 932 is in a palpable position so that the patient and/or another person can feel for the palpable indication of a vessel of the patient.

Figure 9B:
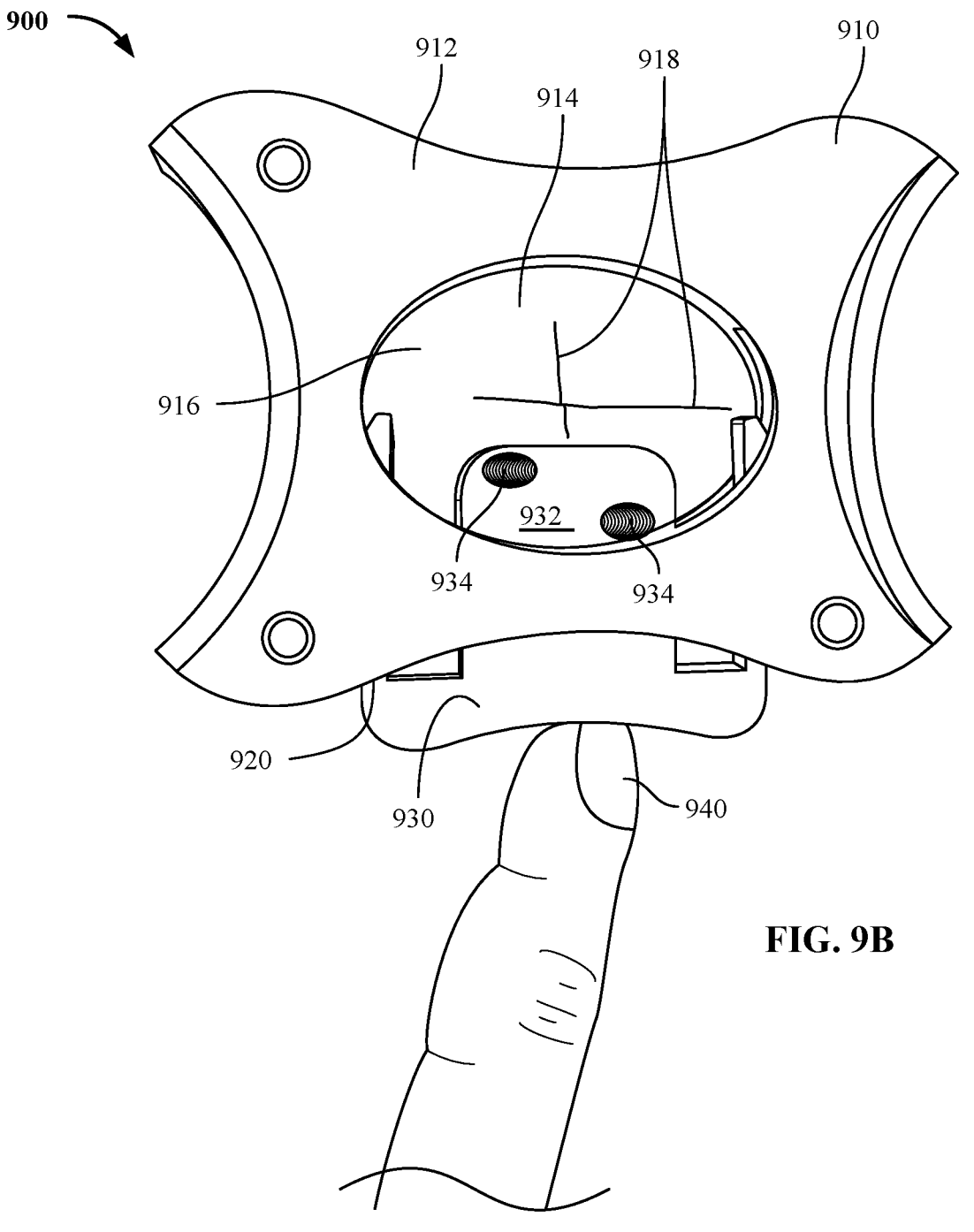
FIG. 9B illustrates an external needle guide with a needle guide slide being positioned for needle insertion.
Figure 9C:
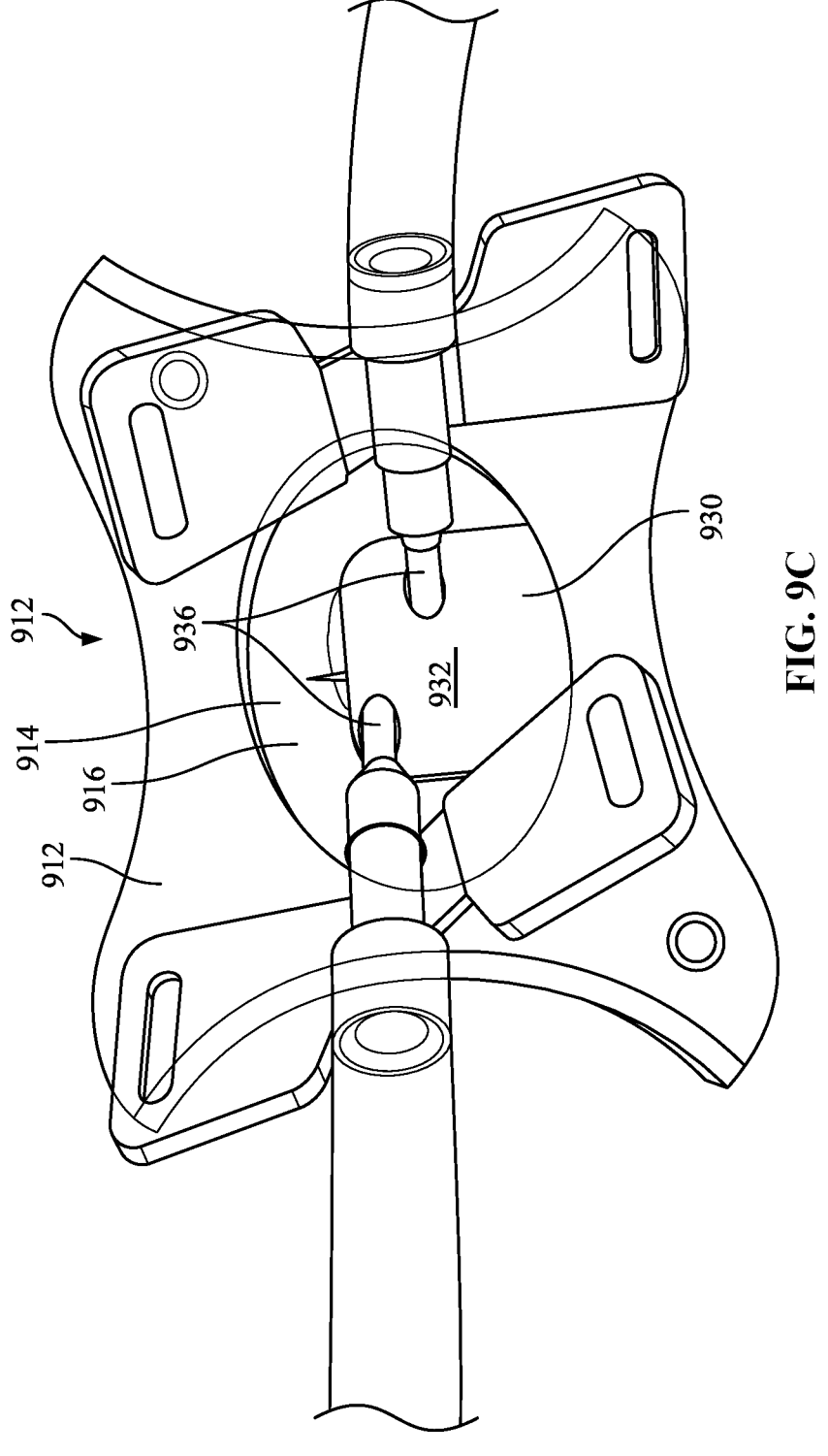
FIG. 9C illustrates an external needle guide with a needle guide slide with two needles inserted into a patient.

FIG. 9B illustrates an external needle guide with a needle guide slide being positioned for needle insertion. FIG. 9C illustrates an external needle guide with a needle guide slide with two needles inserted into a patient. As can be seen in FIG. 9B, the needle guide slide 932 includes two needle apertures 934. In other cases, the needle guide slide 932 may include one or more include needle markers, needle slots, and/or needle notches.

Referring to FIGS. 9A-9C, upon finding the palpable indication of a vessel of the patient and securing the external needle guide 900 to the skin of the patient, the patient and/or another person can move the needle guide slide 932 in a needle insertion position for inserting a needle(s) 936 into the vessel of the patient using their finger 940. In other words, the guide slot 920 enables the needle guide slide 932 to be positioned over the opening 914. In some cases, the needle guide slide 932 can move from the palpable position to the needle insertion position via a track-like mechanism within the guide slot 920. In some cases, the guide slot 920 may include a catch-like mechanism to secure the needle guide slide 932 into the needle insertion position so there is no movement of the needle guide slide 932 during needle insertion. In some cases, the guide slot 920 may include a catch-like mechanism to secure the needle guide slide 932 in the palpable position so there is no movement of the needle guide slide 932 when the patient and/or another person is feeling for the palpable indication of the vessel of the patient.

Once the needle guide slide 932 is placed in the needle insertion position, the patient and/or another person can place needles 936 into the vessel of the patient by using the needle apertures 934, as can be seen in FIG. 9C. The needle guide slide 932 may include one or more needle markers, needle slots, needle notches, and/or needle apertures.

Figure 10A:
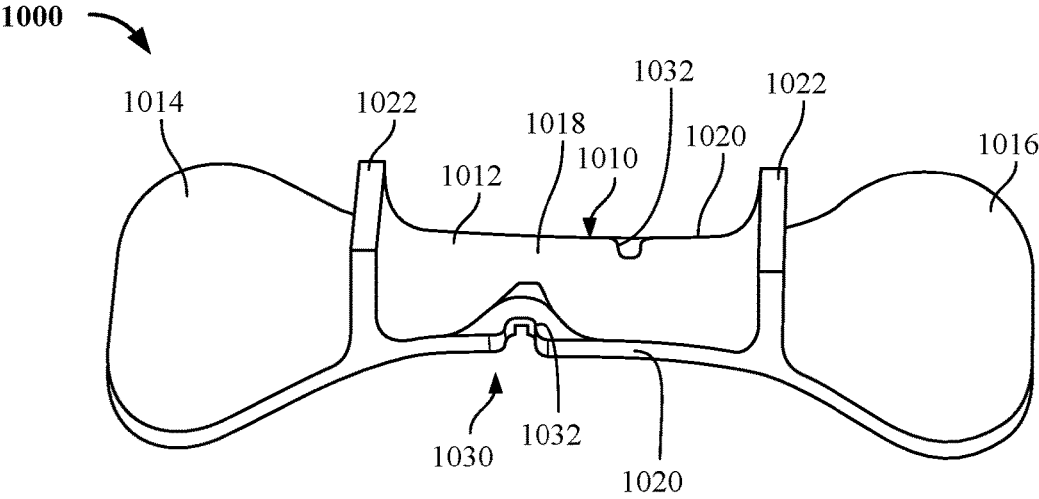
FIG. 10A is an angled view illustrating an example of needle notches along an edge of a body of an external needle guide.
Figure 10B:
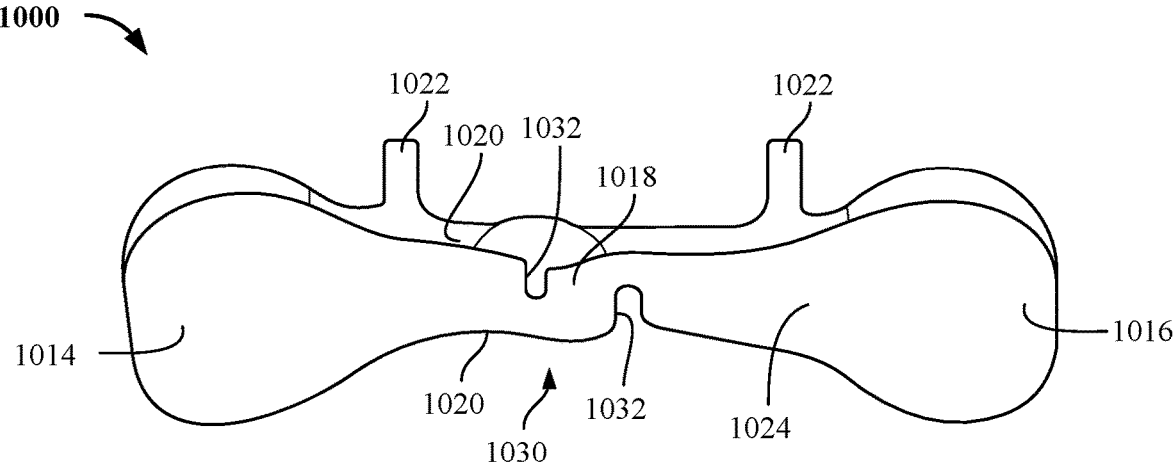
FIG. 10B is a bottom view illustrating an example of needle notches along an edge of a body of the external needle guide of FIG. 10A.

FIG. 10A is an angled view illustrating an example of needle notches along an edge of a body of an external needle guide; and FIG. 10B is a bottom view illustrating an example of needle notches along an edge of a body of the external needle guide of FIG. 10A. The external needle guide 1000 includes a skin contact portion 1010 and a needle guide portion 1030. The skin contact portion 1010 includes an elongated body 1012 with a first end 1014, a second end 1016, and a middle portion 1018. The needle guide portion 1030 includes needle notches 1032 along an edge 1020 of each side of the middle portion 1018 of the elongated body 1012. In some cases, the external needle guide 1000 also includes two grip protrusions 1022 that can be used by a patient and/or another person to pick up and place the external needle guide 1000 into position for needle insertion. It should be understood that the grip protrusions 1022 shown in FIGS. 10A and 10B are merely examples and the specific structure of grip protrusions may vary in other examples.

The bottom portion 1024 of the external needle guide 1000 may include an adhesive for securing the external needle guide 1000 to the skin of the patient. The needle notches 1032 are formed so that a patient and/or another person inserting needles into the vessel of the patient can use the needle notches 1032 to insert the needles at the correct angle relative to the skin of the patient and then tape the body of the needles to the skin of the patient to prevent the needles from being (accidentally) dislodged during dialysis (or any other medical treatment requiring the use of an external needle guide 1000). It should be understood that in other examples, the needle guide portion 1030 of the exter- nal needle guide 1000 may include one or more needle markers, needle slots, and/or needle apertures instead of the needle notches 1032.

Figure 11A:
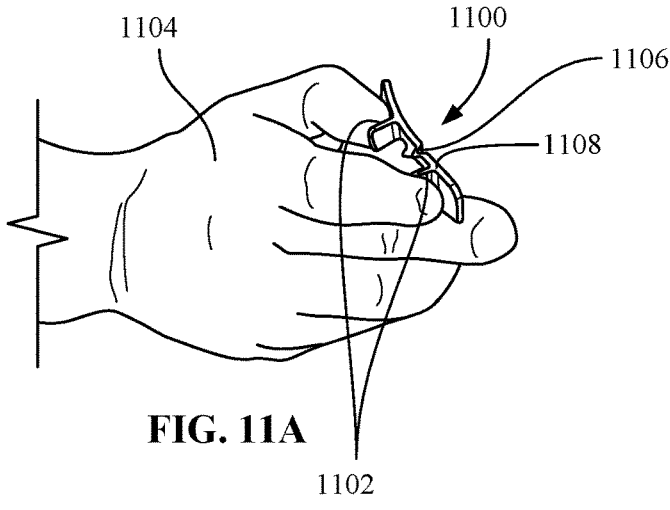
FIGS. 11A-11C illustrate a patient and/or other person finding a vessel, positioning an external needle guide with needle notches along an edge of a body of an external needle guide, and inserting the needles.
Figure 11B:
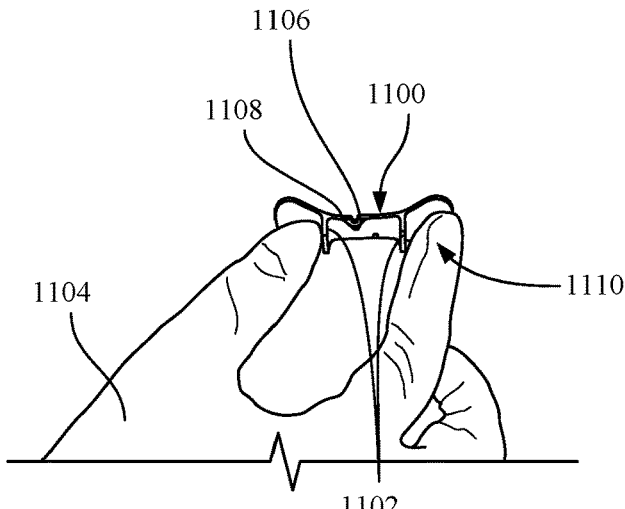
Figure 11C:
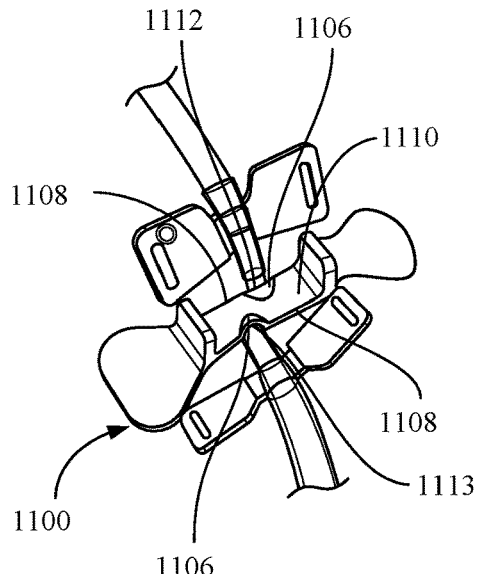

FIGS. 11A-11C illustrate a patient and/or another person finding a vessel, positioning an external needle guide with needle notches along an edge of a body of an external needle guide, and inserting the needles. FIG. 11A illustrates a patient and/or another person feeling for a palpable indica- tion of a vessel. As can be seen, the patient and/or another person can simultaneously hold the external needle guide 1100, via the grip protrusions 1102, and feel for a palpable indication of a vessel of the patient at the same time with one hand 1104. This enables a patient to ensure accurate place- ment of the external needle guide 1100.

FIG. 11B illustrates a patient and/or another person posi- tioning an external needle guide 1100 with one hand 1104 after locating the palpable indication of the vessel of the patient. As can be seen, needle notches 1106 are included for placement of the needle into the vessel of the patient. The needle notches 1106 are positioned along an edge 1108 of a body 1110 of the external needle guide 1100. The needle notches 1106 ensure needles are inserted at a predetermined angle relative to the skin of the patient. In some cases, the needle notches 1106 may include a tapered and/or catch structure to prevent needles from being inserted past a predetermined length.

FIG. 11C illustrates two needles 1112, 1113 inserted into a vessel of a patient via needle notches 1106 of an external needle guide 1100. Each of the needles 1112, 1113 can be inserted with one hand 1104; and due to the needle notches 1106, the needles 1112, 1113 are inserted at the correct angle for a good puncture. In some cases, the external needle guide 1100 can be further supported with an external adhesive (e.g., medical tape). As can be seen, all of these steps can be accomplished with one hand 1104. This enables a patient to cannulate their own vessels.

FIGS. 12A-12H illustrate implementations of external needle anchors with an angle feature and a tubing clip. In some cases, an external needle anchor may be configured to accept only one needle. Referring to FIGS. 12A-H, an external needle anchor 1200 includes a skin contact portion 1210 and a needle anchor portion 1220. The needle anchor portion may (or may not) be used to insert a needle into the vessel; yet in either case, the needle anchor portion 1220 is configured to securely hold a needle 1230 in place once the needle 1230 is inserted into a vessel of a patient, thereby preventing unwanted movement of the needle 1230 that can result in painful damage to the vessel and surrounding area of the patient's body and reducing waste (e.g., layers of tape that have been traditionally used to accomplish similar results). The needle anchor portion 1220 includes a tubing clip 1222, an anchor base feature 1224, and an angle feature 1226 that provides an angle at which a needle 1230 is inserted relative to the skin of the patient.

In some cases, the anchor base feature 1224 provides a structural support that the needle 1230, tubing 1232, and needle wings 1234 can be secured to, preventing any unwanted movement of the needle 1230. The anchor base feature 1224 provides a place for a base of a needle 1230, including wings of a needle 1230, to rest. In some cases, the anchor base feature 1224 can secure the base of the needle 1230 to the needle anchor portion 1220 (e.g., via a contoured fit of the needle 1230 into the anchor base feature 1224, or via strap or some other securing mechanism).

The tubing clip 1222 secures the tubing 1232 in position, which provides additional stability to the needle 1230 to prevent unwanted movement and/or unexpected withdraw- als of the needle 1230 from the vessel of the patient. Indeed, medical tape may not be needed to secure the needle 1230 when a tubing clip 1222 is used.

The angle feature 1226 provides the ability to select or adjust the angle at which the needle 1230 is inserted relative to the skin of the patient. This allows for patients with vessels of all different shapes, sizes, and depths beneath the skin to comfortably utilize external needle anchor 1200. In some cases, as illustrated in FIGS. 12A-12D, the angle feature 1226 is adjustable such that the angle for the insertion of a needle 1230 can be adjusted as needed. In some cases, as illustrated in FIGS. 12E-12H, the angle feature 1226 is fixed at a specific angle.

Figures 12E, 12F, 12G, 12H:
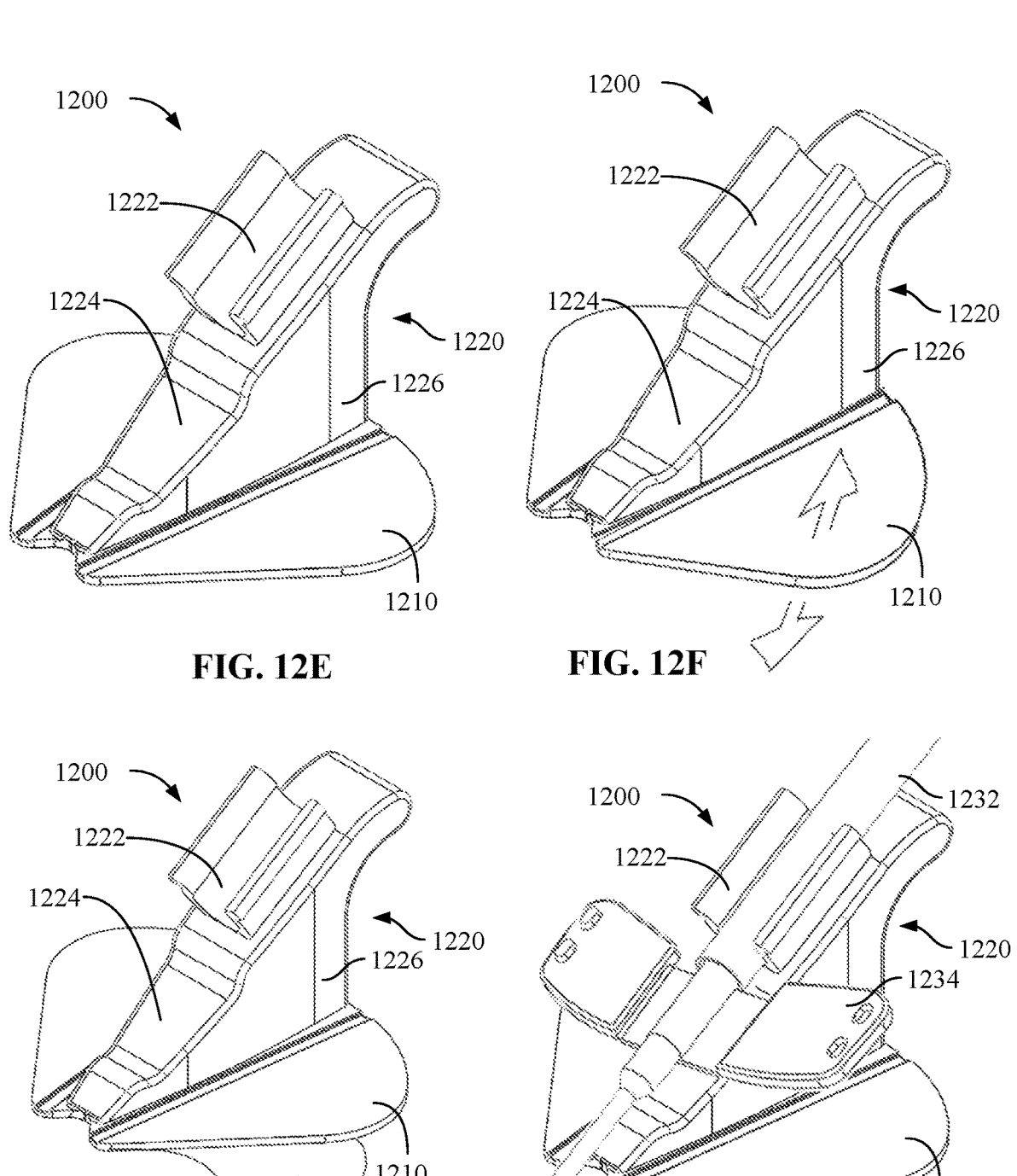

Referring specifically to FIG. 12F, the skin contact portion 1210 is flexible and able to be deformed vertically up or down (as indicated by the arrows). Referring specifically to FIG. 12G, backing 1212 is removed from an adhesive of the skin contact portion 1210.

As mentioned above and as described with respect to FIGS. 12A-12D, the adjustable-type angle feature 1226 can adjust the angle at which the needle 1230 is inserted relative to the skin of the patient by collapsing to decrease the angle and rising to increase the angle. In some cases, a hinge can be provided within the angle feature 1226 close to where the needle 1230 is inserted into the skin of the patient, allowing the collapse and rise of the angle feature 1226. In some of these cases, a snap, latch, and/or locking mechanism can be included to secure the external needle anchor 1200 to the desired angle at which the needle 1230 is inserted relative to the skin of the patient. The snap, latch, and/or locking mechanism can be positioned next to the tubing clip 1222. In some cases, the collapse of the adjustable-type angle feature 1226 can include a removal of material from the angle feature 1226 and the rise of the angle feature 1226 can include an addition of material from the angle feature 1226. In some cases, the rise of the adjustable-type angle feature 1226 can include a ratchet lever (e.g., with each tooth in the gear of the ratchet level increasing the angle by a specified amount) and the collapse of the angle feature 1226 can include a release for the ratchet lever.

Figure 13A:
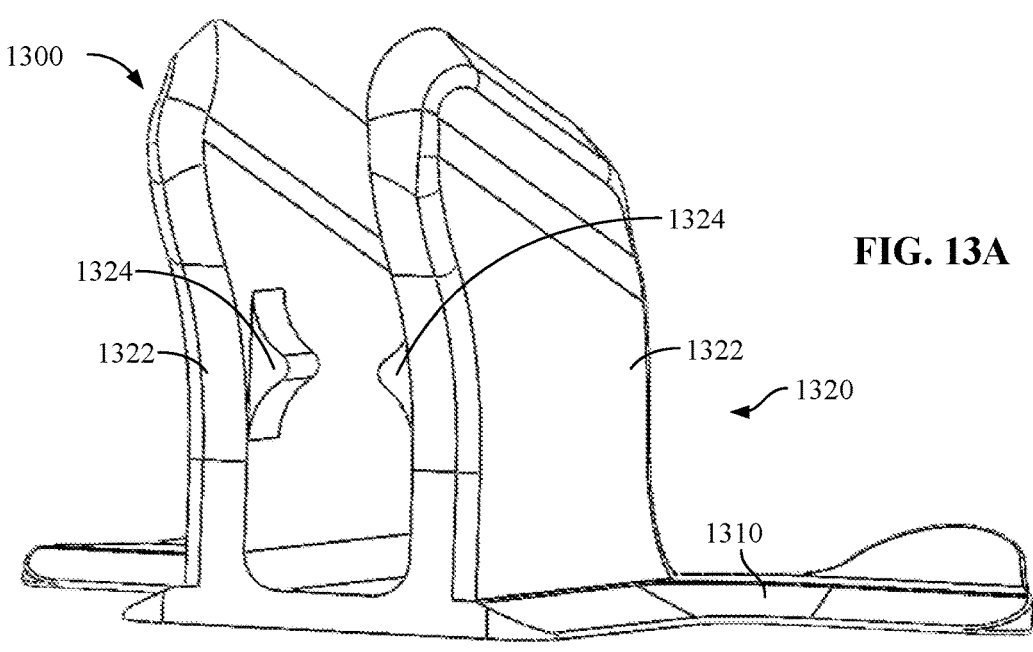
FIGS. 13A-13F illustrate examples of external needle anchors with multiple tubing slots.
Figure 13B:
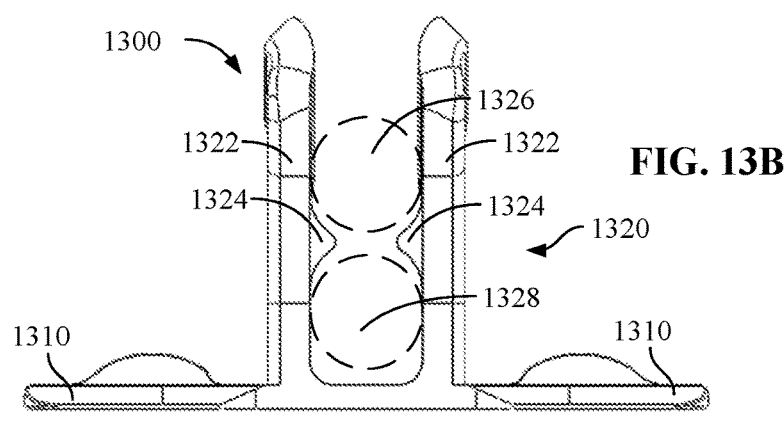
Figure 13C:
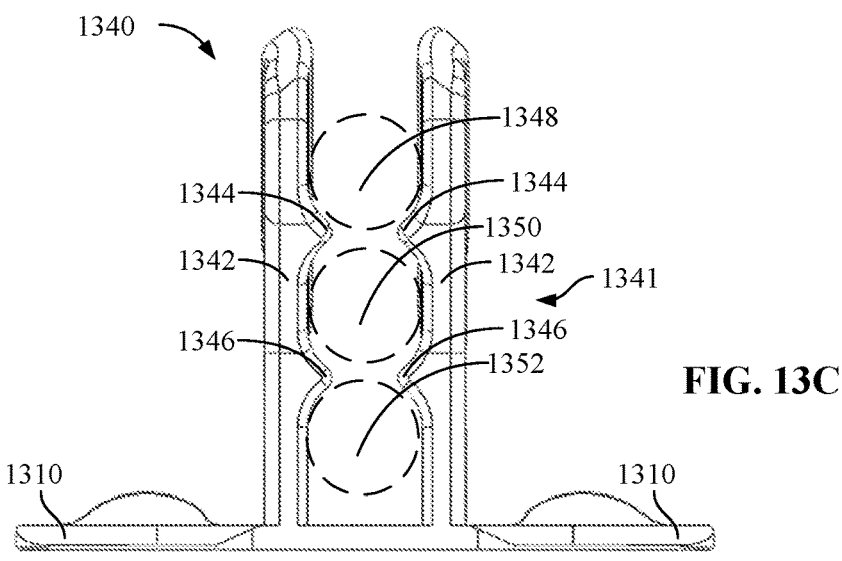

FIGS. 13A-13F illustrate examples of external needle anchors with multiple tubing slots. Referring to FIGS. 13A and 13B, an external needle anchor 1300 includes a skin contact portion 1310 and a needle anchor portion 1320. The needle anchor portion 1320 includes a parallel anchor base feature 1322. The parallel anchor base feature 1322 includes a set of tubing dividers 1324 that form two tubing slots 1326, 1328 within the parallel anchor base feature 1322. Referring to FIG. 13C, an external needle anchor 1340 includes a skin contact portion 1310 and a needle anchor portion 1341. The needle anchor portion 1341 includes a parallel anchor base feature 1342. The parallel anchor base feature 1342 includes two sets of tubing dividers 1344, 1346 that form three tubing slots 1348, 1350, 1352 within the parallel anchor base feature 1342.

Referring to FIGS. 13A-13F, each tubing slot 1326, 1328, 1348, 1350, 1352 secures the tubing 1362 in position, which provides additional stability to the needle 1360 to prevent unwanted movement and/or unexpected withdrawals of the needle 1360 from the vessel of the patient. Indeed, medical tape may not be needed to secure the needle 1360 when a tubing slot 1326, 1328, 1348, 1350, 1352 is used. Furthermore, each tubing slot 1326, 1328, 1348, 1350, 1352 adjusts the angle of the needle 1360 with respect to the surface of the skin of the patient.

Figures 13D, 13E, 13F:
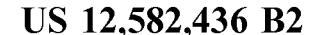

Referring to FIG. 13D, the needle is shown in a top tubing slot (e.g., tubing slot 1326 of FIGS. 13A and 13B or tubing slot 1348 of FIG. 13C), which creates a relatively large/steep angle with respect to the surface of the patient's skin. The top tubing slot 1326, 1348 may be used when a patient's vessel is relatively deep below the surface of the patient's skin and/or when the needle 1360 is relatively short. Referring to FIG. 13E, the needle is shown in a middle tubing slot (e.g., tubing slot 1350 of FIG. 13C), which creates a moderate angle with respect to the surface of the patient's skin. The middle tubing slot 1350 may be used when a patient's vessel has an average depth below the surface of the patient's skin. Referring to FIG. 13F, the needle is shown in a bottom tubing slot (e.g., tubing slot 1328 of FIGS. 13A and 13B or tubing slot 1352 of FIG. 13C), which creates a relatively small/shallow angle with respect to the surface of the patient's skin. The bottom tubing slot 1328, 1352 may be used when a patient's vessel is relatively deep below the surface of the patient's skin and/or when the needle 1360 is relatively long. It should be understood that external needle anchors 1300, 1340 having a plurality of tubing slots provide similar functionality (e.g., varying angles for needles) as the angle feature 1226 described above with respect to FIGS. 12A-12D. Indeed, each of the plurality of tubing slots may be said to have a different predetermined angle relative to the skin of the patient.

Referring to FIGS. 13D-13F, the parallel anchor base features 1322, 1342 also include front edges 1330, 1370 that are sloped towards the skin contact portion 1310 to provide a structure for the needle wings 1364 to securely rest against.

Figure 14A:
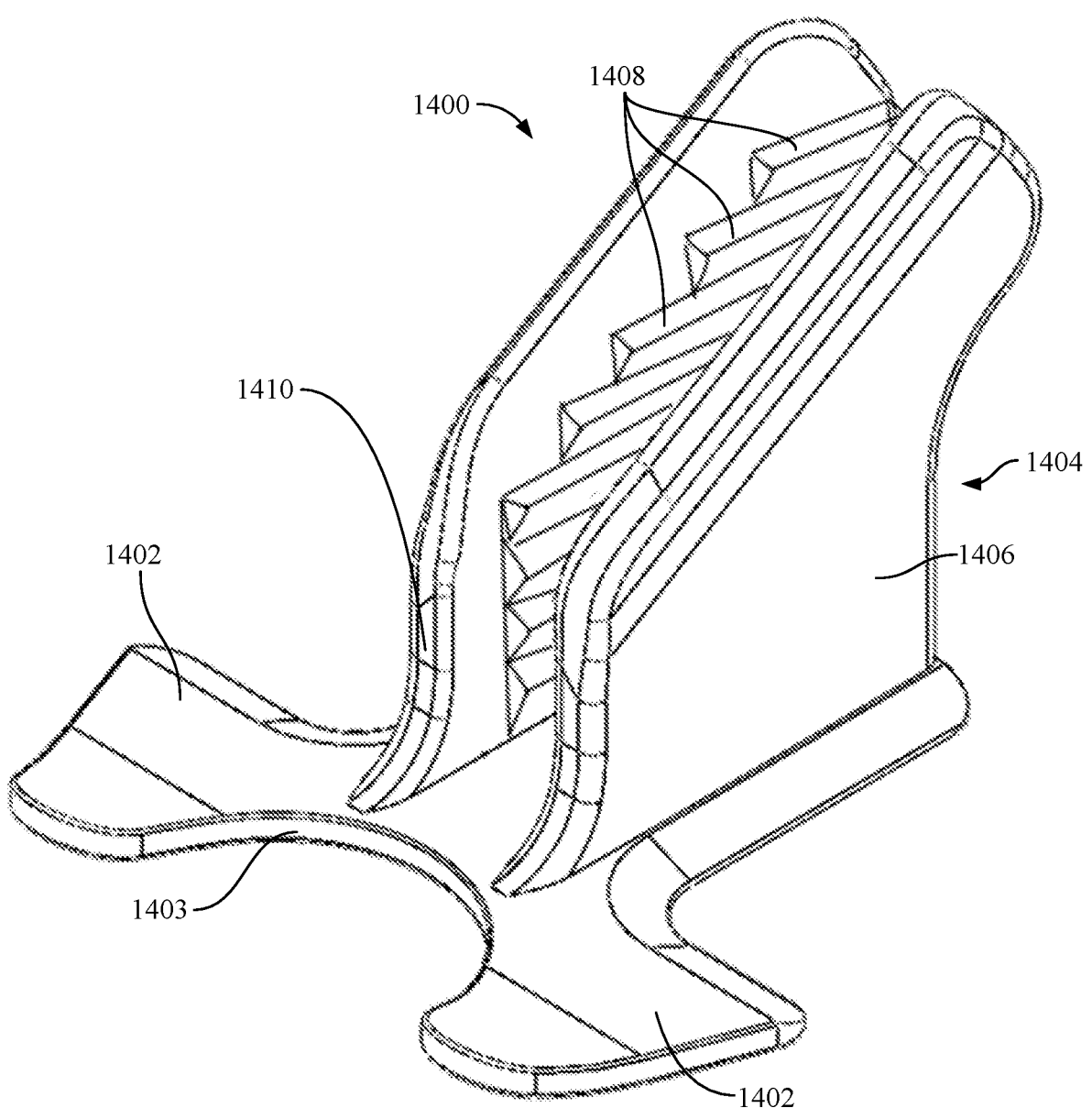
FIGS. 14A-14C illustrate examples of external needle anchors with a ridged tubing slot.
Figure 14B:
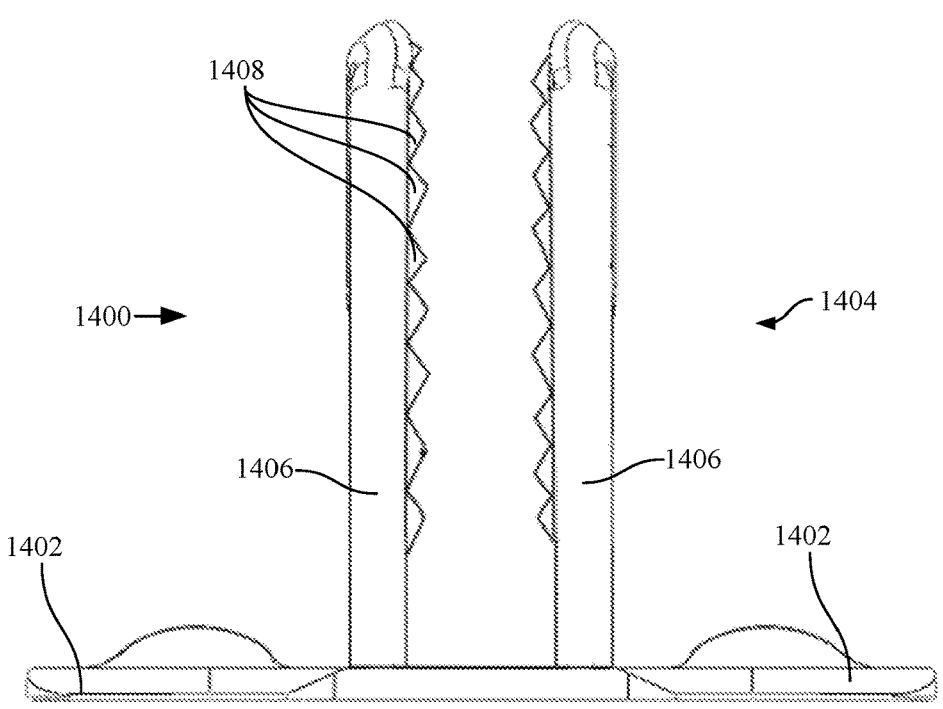
Figure 14C:
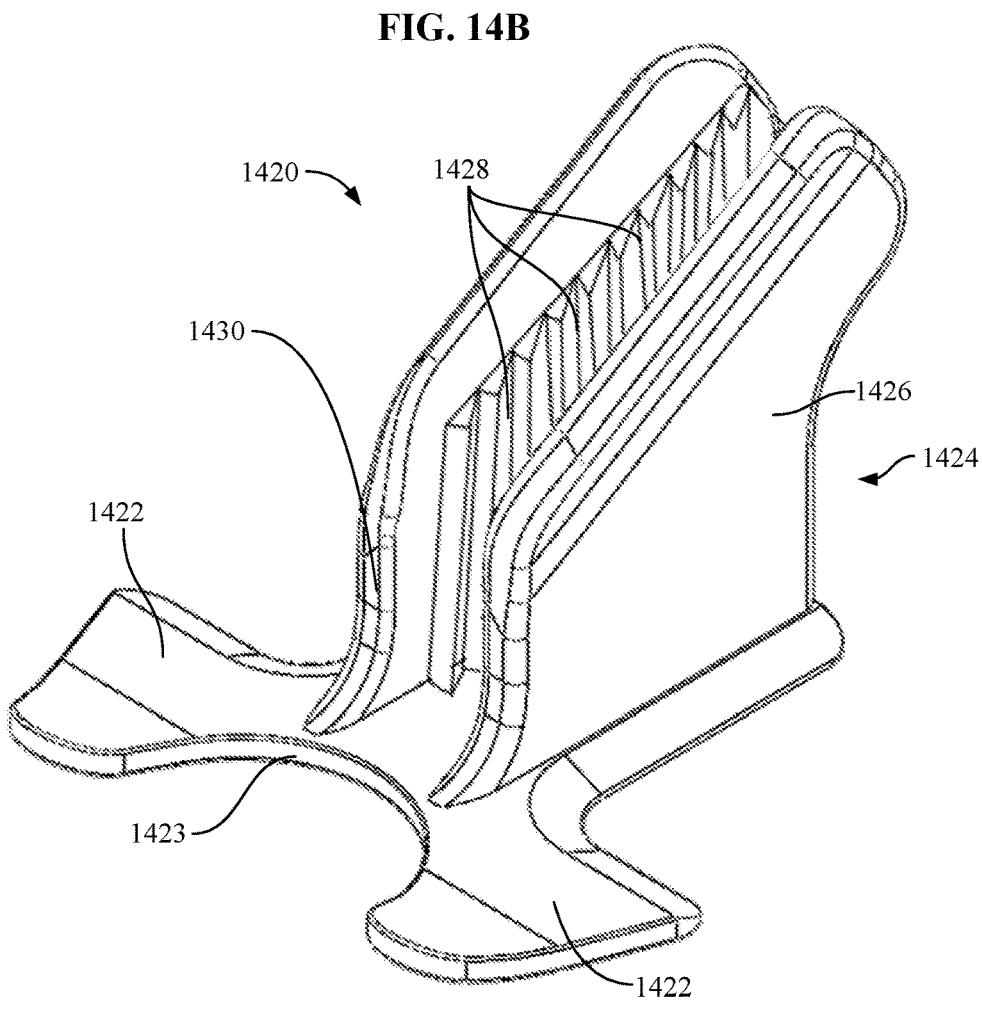

FIGS. 14A-14C illustrate examples of external needle anchors with a ridged tubing slot. Referring to FIGS. 14A-14C, external needle anchors 1400, 1420 include a skin contact portion 1402, 1422 and a needle anchor portion 1404, 1424. The skin contact portion 1402, 1422 includes an arcuate edge 1403, 1423 for inserting a needle through the skin of a patient and into the vessel of the patient. The needle anchor portion 1404, 1424 includes a parallel anchor base feature 1406, 1426 that includes a plurality of ridges 1408, 1428 on an inner surface for securing/gripping tubing (that is coupled to a needle). The parallel anchor base features 1406, 1426 also include front edges 1410, 1430 that are sloped towards the skin contact portion 1402 to provide a structure for needle wings of a needle to securely rest against. Referring to FIGS. 14A and 14B, the ridges 1408 are positioned (with lines at intervals) parallel to skin of the patient/the skin contact portion 1402. Referring to FIG. 14C, the ridges 1428 are positioned (with lines at intervals) perpendicular to skin of the patient/the skin contact portion 1422. In some cases, the plurality of ridges 1408, 1428 may be positioned in any direction that is useful for securing/gripping tubing (that is coupled to a needle). In some cases, the plurality of ridges 1408, 1428 may be used in conjunction with and/or positioned in line with an angle feature (e.g., tubing divider 1324 of FIGS. 13A and 13B and/or tubing dividers 1344, 1346 of FIG. 13C).

Figures 15A, 15B, 15C:
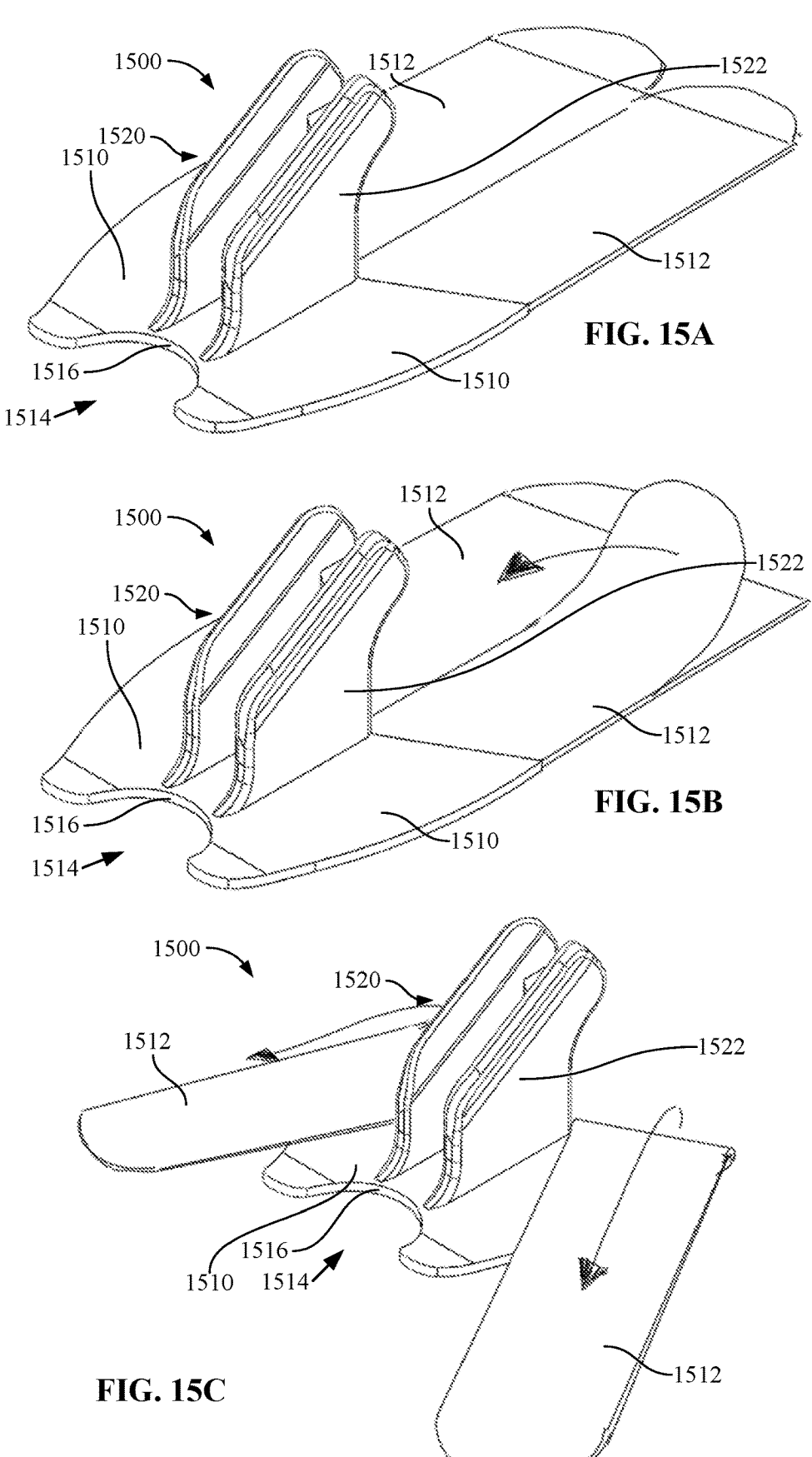
FIGS. 15A-15C illustrate an example of an external needle anchor with fold-over skin contact portions.

FIGS. 15A-15C illustrate an example of an external needle anchor with fold-over skin contact portions. Referring to FIGS. 15A-15C, an external needle anchor 1500 includes a skin contact portion 1510 and a needle anchor portion 1520. The skin contact portion 1510 includes a folding adhesive feature 1512 that can fold towards the insertion area 1514 of the skin contact portion 1510. The insertion area 1514 is the area of the skin contact portion 1510 that is closest to an insertion point of a needle. As illustrated, insertion area 1514 includes an arcuate edge 1516 around the insertion point of the needle. In some cases, the insertion area 1514 may include edges of varying curvatures/dimensions. As with most needle anchors 1500, the needle anchor portion 1520 includes an anchor base feature 1522.

Figures 16A, 16B:
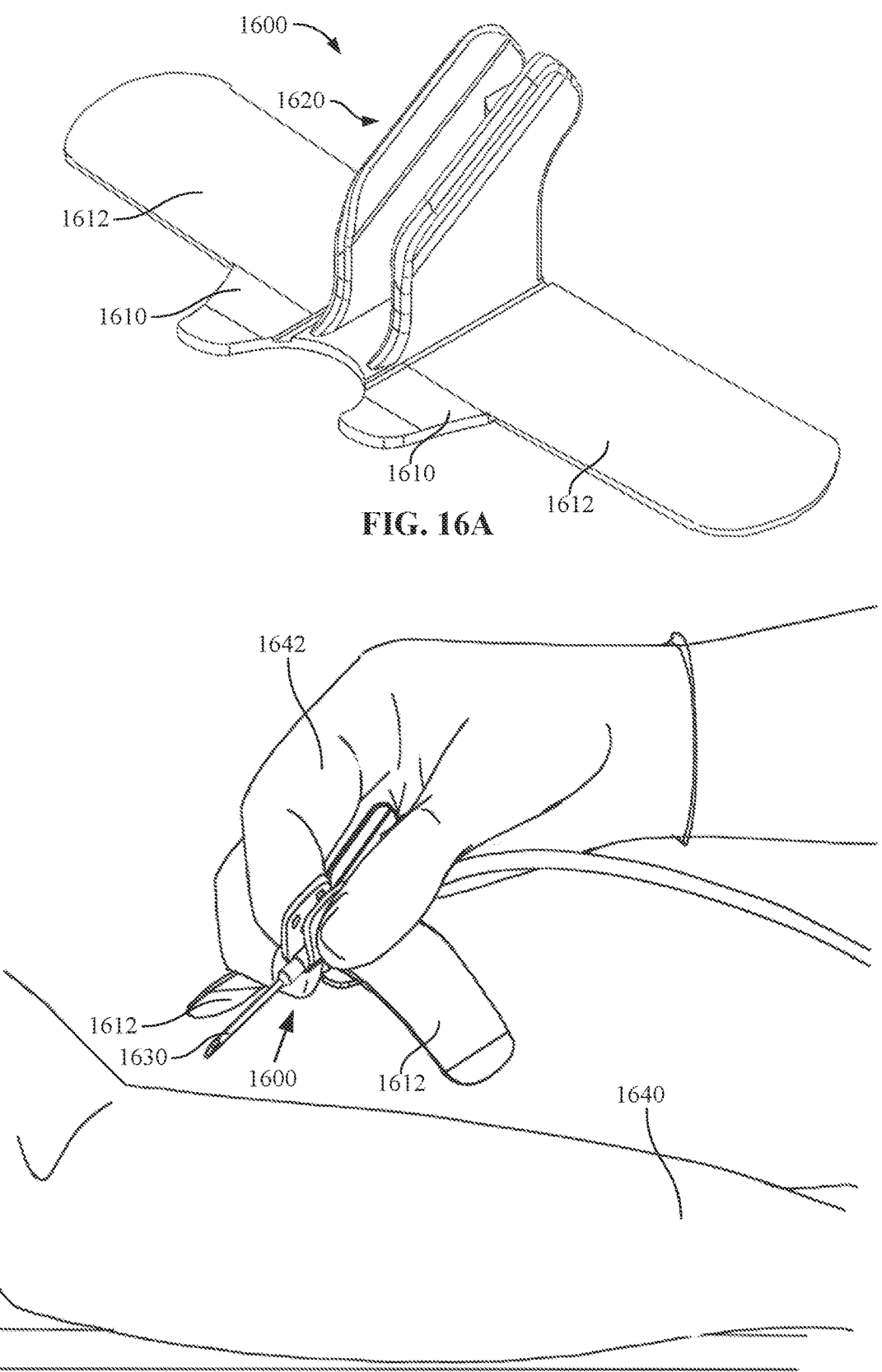
FIGS. 16A-16C illustrate an example of an external needle anchor with elliptical wing feature.
Figure 16C:
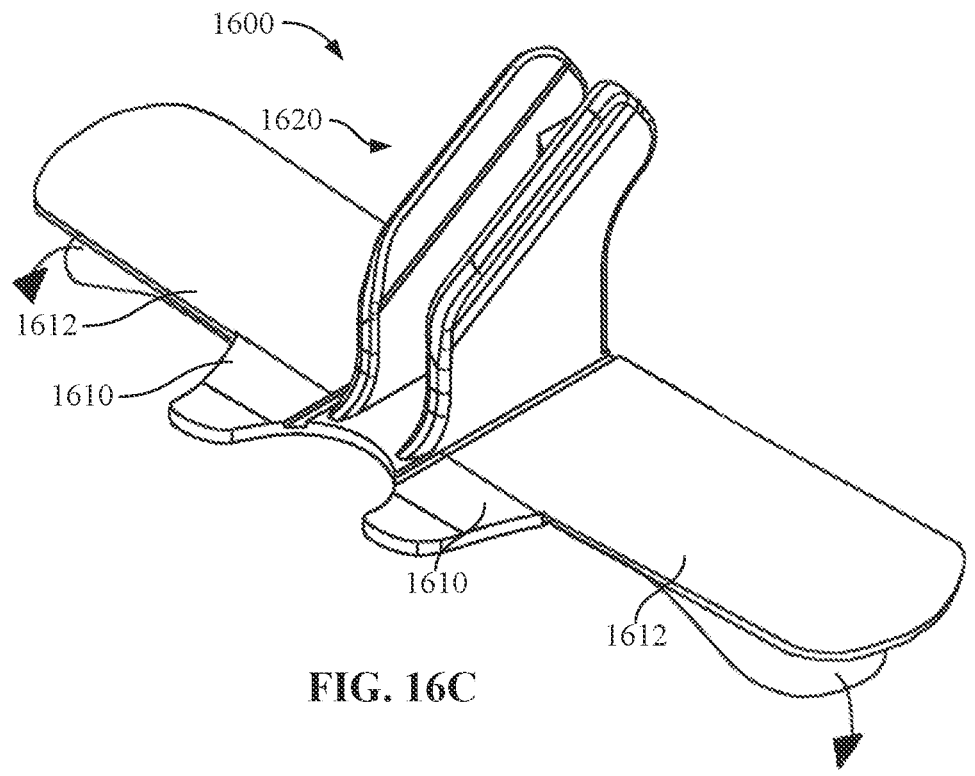

FIGS. 16A-16C illustrate an example of an external needle anchor with elliptical wing feature. Referring to FIGS. 16A-16C, an external needle anchor 1600 includes a skin contact portion 1610 and a needle anchor portion 1620. The needle anchor portion 1620 includes a parallel anchor base feature 1622 (as described above with respect to FIGS. 13A-15C). The skin contact portion 1610 includes an elliptical wing feature 1612. The elliptical wing feature 1612 extend horizontally from the needle anchor portion 1620. Referring to FIG. 16B, the patient (or other person) has secured/anchored a needle 1630 to the external needle anchor 1600 via the needle anchor portion 1620 prior to inserting the needle 1630 into the patient's arm 1640. Referring to FIGS. 16B and 16C, the elliptical wing feature 1612 is flexible to allow for better grip in the patient's hand 1642. Indeed, the flexible material of the elliptical wing feature 1612 provides a patient the ability to self-cannulate in their own arm 1640 when the needle 1630 is secured/anchored to the external needle anchor 1600 prior to insertion of the needle into a vessel.

Figures 17A, 17B:
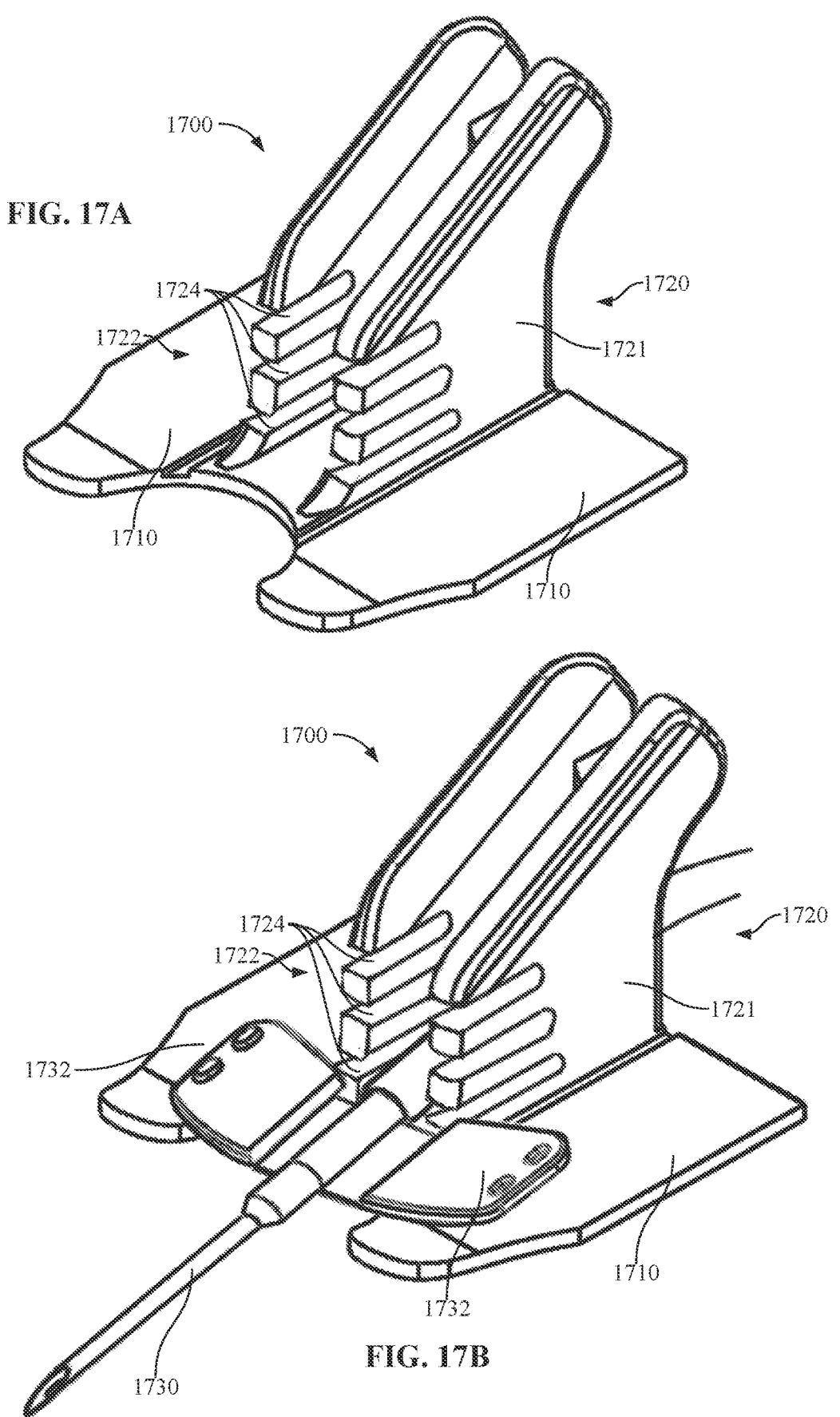
FIGS. 17A-17C illustrate an example of an external needle anchor with needle wing slots in an anchor base feature.
Figure 17C:
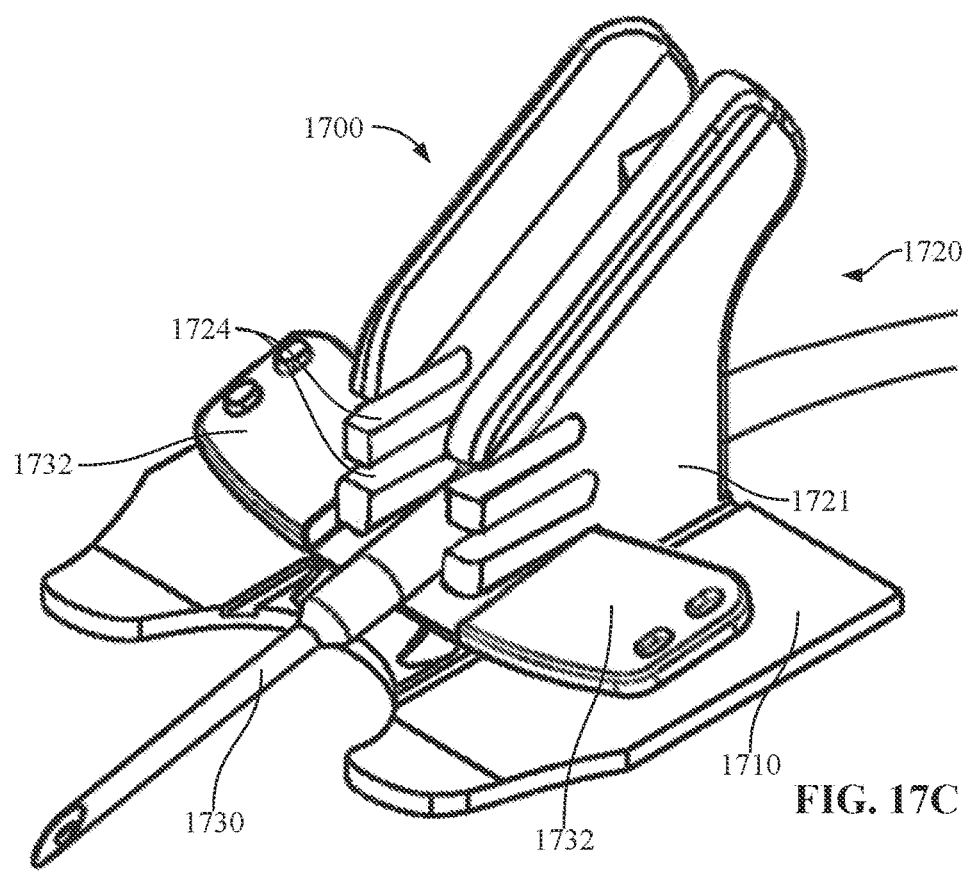

FIGS. 17A-17C illustrate an example of an external needle anchor with needle wing slots in an anchor base feature. Referring to FIGS. 17A-17C, an external needle anchor 1700 includes a skin contact portion 1710 and a needle anchor portion 1720. The needle anchor portion 1720 includes a parallel anchor base feature 1721. The parallel anchor base feature 1721 includes front edges 1722 that are sloped towards the skin contact portion 1710 and has a plurality of corresponding slots 1724 that, as illustrated in FIG. 17C, are shaped to house a set of needle wings 1732 of a needle 1730. In other words, each corresponding slot 1724 provides the ability to secure/anchor the needle wings 1732 of a needle 1730. Furthermore, each of the corresponding slots 1724 provide a different angle (with respect to the skin of a patient) to secure/anchor the needle wings 1732 of the needle 1730. For example, as illustrated in FIG. 17C, the needle wings 1732 of the needle 1730 are secured/anchored in a bottom corresponding slot 1724 that corresponds to a relatively small angle relative to the skin of a patient.

Figure 18A:
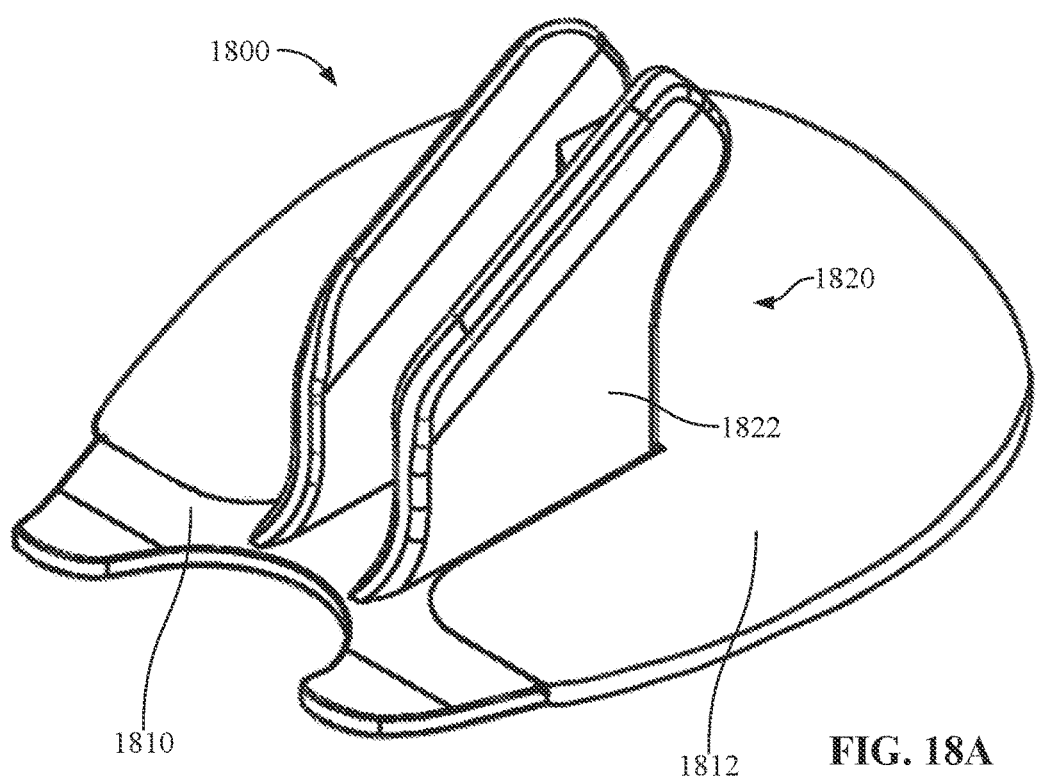
FIGS. 18A-18B illustrate an example of an external needle anchor with an oval shaped skin contact portion.
Figure 18B:
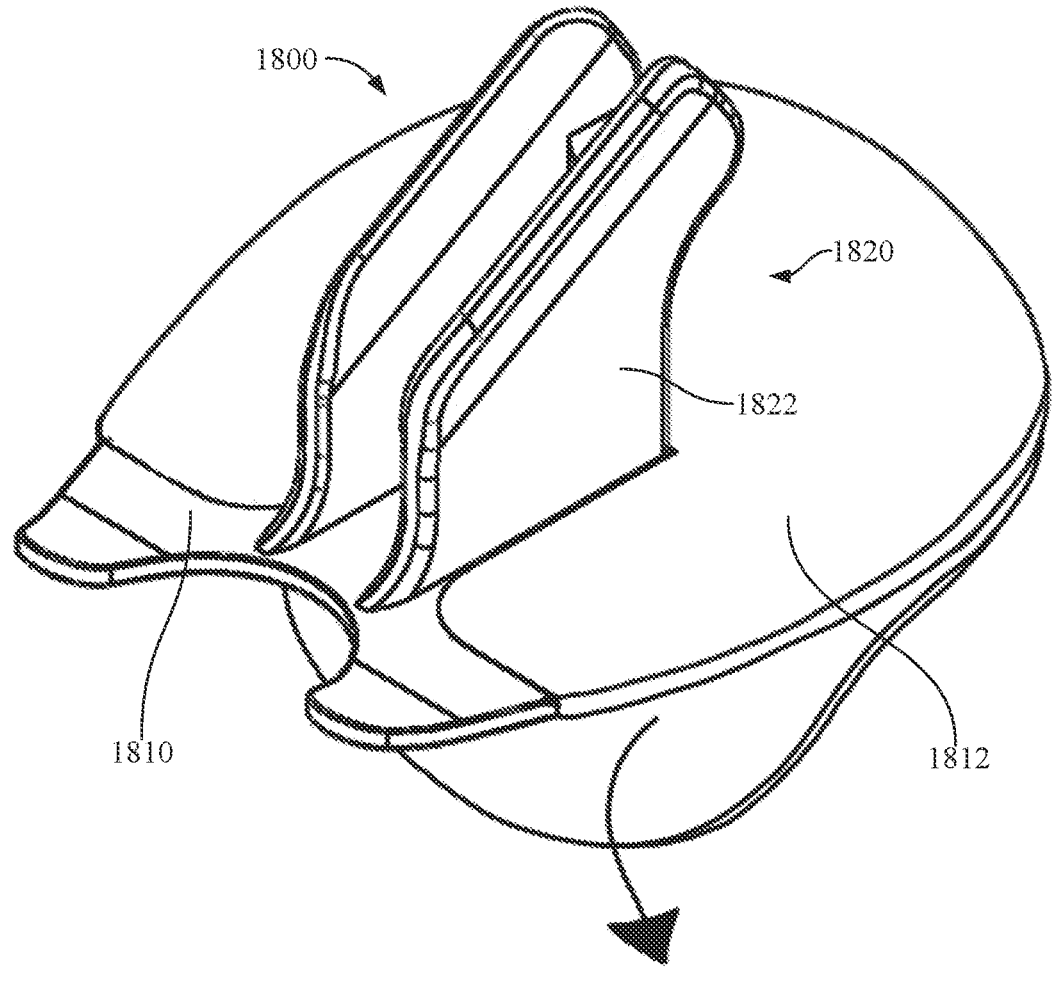

FIGS. 18A-18B illustrate an example of an external needle anchor with an oval shaped skin contact portion. Referring to FIGS. 18A and 18B, an external needle anchor 1800 includes a skin contact portion 1810 and a needle anchor portion 1820. The needle anchor portion includes an anchor base feature 1822. The skin contact portion 1810 includes an ovular shaped wing 1812. As illustrated in FIG. 18B, the ovular shaped wing 1812 may be made of flexible material to attached to skin of a patient that is rounded and/or not flat (e.g., the inside of an elbow).

FIGS. 19A-19H illustrate examples of external needle guides/anchors with an angle feature, a needle slot, and a tubing clip. Indeed, these Figures are referred to as external needle "guides/anchors" because they contain a plurality of features that guide a needle into a vessel for a good puncture and a plurality of features that anchor the needle to the external needle guide/anchor itself (e.g., without the use of medical tape). Referring to FIGS. 19A-19H, an external needle guide 1900 includes a skin contact portion 1910 and a needle guide portion 1920. The needle guide portion 1920 includes a tubing clip 1922, an anchor base feature 1924, a needle slot 1926, and an angle feature 1928 that provides an angle at which a needle 1930 is inserted relative to the skin of a patient. In some cases, the angle feature 1928 is adjustable such that the angle at which the needle 1930 is inserted relative to the skin of a patient can be adjusted as needed.

In some cases, the needle slot 1926 secures/anchors the needle 1930 to prevent unwanted and/or unexpected withdrawals of the needle 1930, as well guides the needle 1930 into the vessel. The tubing clip 1922 provides additional stability to secure/anchor the needle 1930 and tubing 1932 to prevent unwanted and/or unexpected withdrawals of the needle 1930 from the vessel of the patient. In some cases, the needle slot 1926 can prevent the needle 1930 from being inserted further than intended by a patient and/or another person by abutting the bushing 1934 of the needle 1930. In other words, the needle bushing 1934 has a larger diameter than the needle slot 1926 will allow to pass, preventing the needle 1930 from being inserted further than intended by a patient and/or another person. In some cases, the needle slot 1926 can prevent the needle 1930 from being inserted further than intended by a patient and/or another person by abutting the wings 1936 of the needle 1930. These are features that help guide the needle 1930 into the vessel of the patient for a good puncture.

Referring specifically to FIGS. 19A-19D, the angle feature 1928 is shown at a maximum angle relative to the skin of the patient. As explained above, when the patient wishes to access a vessel that is relatively far from the surface of the patient's skin, the patient and/or another person can either select a needle guide with a fixed angle feature 1928 of a desired angle or adjust a needle guide with an adjustable angle feature 1928 to a larger angle. In some cases, the maximum angle relative to the skin of the patient is ninety degrees. In other cases, the maximum angle relative to the skin is less than ninety degrees. For example, in the illustrated embodiment, the maximum angle is 45 degrees.

Referring specifically to FIGS. 19E-19H, the adjustable angle feature 1928 is shown at a minimum angle relative to the skin of the patient. As explained above, when the patient wishes to access a vessel that is relatively close to the surface of the patient's skin, the patient and/or another person can either select a needle guide with a fixed angle feature 1928 of a desired angle or adjust a needle guide with an adjustable angle feature 1928 to a smaller angle. In some cases, the minimum angle relative to the skin of the patient is five degrees. In some cases, the minimum angle is 20 degrees.

Referring again to FIGS. 19A-19H, in some cases, the angle feature 1928 can be an adjustable-type that enables a user to adjust angles every one degree between the minimum and the maximum angles relative to the skin of the patient. In some cases, the angle feature 1928 can be an adjustable-type that enables a user to adjust angles every five degrees between the minimum and the maximum angles relative to the skin of the patient. In some cases, the angle feature 1928 can be an adjustable-type that enables a user to adjust angles every ten degrees between the minimum and the maximum angles relative to the skin of the patient. In some cases, the angle feature 1928 can be an adjustable-type that enables a user to adjust to any angle between the minimum and the maximum angles relative to the skin of the patient (e.g., through a hinge and an angle locking mechanism). In some cases, an external needle guide has a fixed angle feature 1928. In other words, in some cases, the angle relative to the skin of a patient in which a needle will be inserted can be fixed on an external needle guide. As an example, the external needle guide may come in several different fixed angles for the fixed angle feature 1928 to accommodate certain depths of vessels. Specifically, in some cases, a 20 degree fixed angle feature would accommodate a vessel depth of less than 5 mm, a 30 degree fixed angle feature would accommodate a vessel depth of 5-10 mm, a 40 degree fixed angle feature would accommodate a vessel depth of 10-15 mm, and a 45 degree fixed angle feature would accommodate a vessel depth of greater than 15 mm deep. In some of these cases, the external needle guide/anchor may also include a tubing clip, tubing slot, and/or needle slot.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. An external needle anchor, comprising:
a skin contact portion for securely attaching to skin of a patient; and
a needle anchor portion for securely holding a needle in place once inserted into a vessel of a patient, wherein the needle anchor portion comprises a base at the skin contact portion and a first side wall parallel to a second side wall that forms a plurality of tubing slots for securing a tubing coupled to the needle, the first side wall and the second side wall extending vertically with a non-adjoining gap therebetween from the base extending through ends of the first side wall and the second side wall that are distal to the skin contact portion, each tubing slot having a different predetermined angle relative to the skin of the patient.

2. The external needle anchor of claim 1, wherein the skin contact portion comprises an adhesive.

3. The external needle anchor of claim 2, wherein a portion of the adhesive of the skin contact portion is configured to be folded towards the needle once inserted into the vessel of the patient for securely attaching to the skin of the patient.

4. The external needle anchor of claim 2, wherein the adhesive of the skin contact portion comprises wings that extend horizontally from the needle anchor portion.

5. The external needle anchor of claim 2, wherein the adhesive of the skin contact portion comprises an ovular shape.

6. The external needle anchor of claim 1, wherein the skin contact portion comprises an arcuate edge for inserting the needle through the skin of the patient and into the vessel of the patient.

7. The external needle anchor of claim 1, wherein during use, after the needle is inserted into the vessel of the patient, a tubing slot of the plurality of tubing slots is configured to securely receive the tubing coupled to the needle.

8. The external needle anchor of claim 1, wherein the needle anchor portion further comprises a front edge that is sloped towards the skin contact portion to provide structure for needle wings of the needle to securely rest against.

9. The external needle anchor of claim 1, wherein the needle anchor portion is open to receive the tubing coupled to the needle after insertion of the needle into the vessel of the patient.

* * * * *